US009744311B2

(12) United States Patent
Streit et al.

(10) Patent No.: US 9,744,311 B2
(45) Date of Patent: Aug. 29, 2017

(54) INJECTION DEVICE WITH DOSE DISPLAY FOR SIGNALING THE END OF THE INJECTION

(71) Applicant: TecPharma Licensing AG, Burgdorf (CH)

(72) Inventors: Ursina Streit, Schönbühl (CH); Susanne Schenker, Langenthal (CH)

(73) Assignee: TecPharma Licensing AG, Burgdorf (CH)

( * ) Notice: Subject to any disclaimer, the term of this patent is extended or adjusted under 35 U.S.C. 154(b) by 142 days.

(21) Appl. No.: 14/599,269

(22) Filed: Jan. 16, 2015

(65) Prior Publication Data

US 2015/0133869 A1    May 14, 2015

Related U.S. Application Data

(63) Continuation of application No. PCT/CH2013/000125, filed on Jul. 11, 2013.

(30) Foreign Application Priority Data

Aug. 1, 2012  (EP) ..................................... 12178916

(51) Int. Cl.
*A61M 5/00* (2006.01)
*A61M 5/315* (2006.01)
(Continued)

(52) U.S. Cl.
CPC ............ *A61M 5/3157* (2013.01); *A61M 5/20* (2013.01); *A61M 5/3155* (2013.01);
(Continued)

(58) Field of Classification Search
CPC .......... A61M 5/31501; A61M 5/31525; A61M 5/31528; A61M 5/3153; A61M 5/31533;
(Continued)

(56) References Cited

U.S. PATENT DOCUMENTS 6,004,297 A * 12/1999 Steenfeldt-Jensen ... A61M 5/31551
604/207
9,457,154 B2 * 10/2016 Moller ................ A61M 5/3155
(Continued)

FOREIGN PATENT DOCUMENTS

CH      700404      8/2010
DE    19819409    11/1999
(Continued)

OTHER PUBLICATIONS

PCT International Search Report mailed Oct. 18, 2013 for Application No. PCT/CH2013/000125 (5 pages).

*Primary Examiner* — Kevin C Sirmons
*Assistant Examiner* — William Carpenter
(74) *Attorney, Agent, or Firm* — Dorsey & Whitney LLP; Stuart R. Hemphill, Esq.

(57) ABSTRACT

Drive and metering devices for injection devices include a dose display element with a helical dosage scale; an indicating means; a metering member, which can be rotated relative to the indicating means for dose setting; a discharge spring and an advancement member. The dose display element can be screwed relative to the indicating means about a longitudinal axis (L) and a value on the dose scale can be read via the indicating means corresponding to the set dose. The discharge spring causes the advancement member to discharge the product as it moves an overall discharge stroke length (Hg), where the overall discharge stroke length (Hg) comprises a first partial discharge stroke length (H1), during which the dose display element is rotationally secured in relation to the indicating means and where the dose display element can be rotated relative to the indicating means following the first partial discharge stroke length (H1).

17 Claims, 18 Drawing Sheets

(51) Int. Cl.
*A61M 5/20* (2006.01)
*A61M 5/31* (2006.01)

(52) U.S. Cl.
CPC .... *A61M 5/31541* (2013.01); *A61M 5/31585* (2013.01); *A61M 5/31593* (2013.01); *A61M 5/31553* (2013.01); *A61M 5/31568* (2013.01); *A61M 2005/2026* (2013.01); *A61M 2005/3126* (2013.01); *A61M 2205/581* (2013.01); *A61M 2205/582* (2013.01); *A61M 2205/583* (2013.01)

(58) Field of Classification Search
CPC .......... A61M 5/31545; A61M 5/31548; A61M 5/3155; A61M 5/31553; A61M 5/31556; A61M 5/31558; A61M 5/31563; A61M 5/3157
See application file for complete search history.

(56) References Cited

U.S. PATENT DOCUMENTS

| | | | | |
|---|---|---|---|---|
| 2004/0210199 A1* | 10/2004 | Atterbury | ......... | A61M 5/31566 604/224 |
| 2006/0153693 A1* | 7/2006 | Fiechter | ............ | A61M 5/31553 417/63 |
| 2006/0184117 A1* | 8/2006 | Knight | .................... | A61M 5/24 604/135 |
| 2009/0012479 A1* | 1/2009 | Moller | ................ | A61M 5/3155 604/211 |
| 2010/0268171 A1* | 10/2010 | Moller | .............. | A61M 5/31551 604/246 |
| 2011/0208125 A1* | 8/2011 | Larsen | .................... | A61M 5/24 604/189 |
| 2015/0018771 A1* | 1/2015 | Schenker | ................ | A61M 5/20 604/189 |
| 2015/0018772 A1* | 1/2015 | Schenker | ................ | A61M 5/20 604/189 |
| 2015/0018776 A1* | 1/2015 | Schenker | ............ | A61M 5/2033 604/207 |
| 2016/0184530 A1* | 6/2016 | Schenker | ................ | A61M 5/20 604/211 |

FOREIGN PATENT DOCUMENTS

| | | |
|---|---|---|
| WO | WO 2006/079481 | 8/2006 |
| WO | WO 2009/039851 | 4/2009 |
| WO | WO 2009/105909 | 9/2009 |
| WO | WO 2010/023303 | 3/2010 |
| WO | WO 2012/032411 | 3/2012 |

* cited by examiner

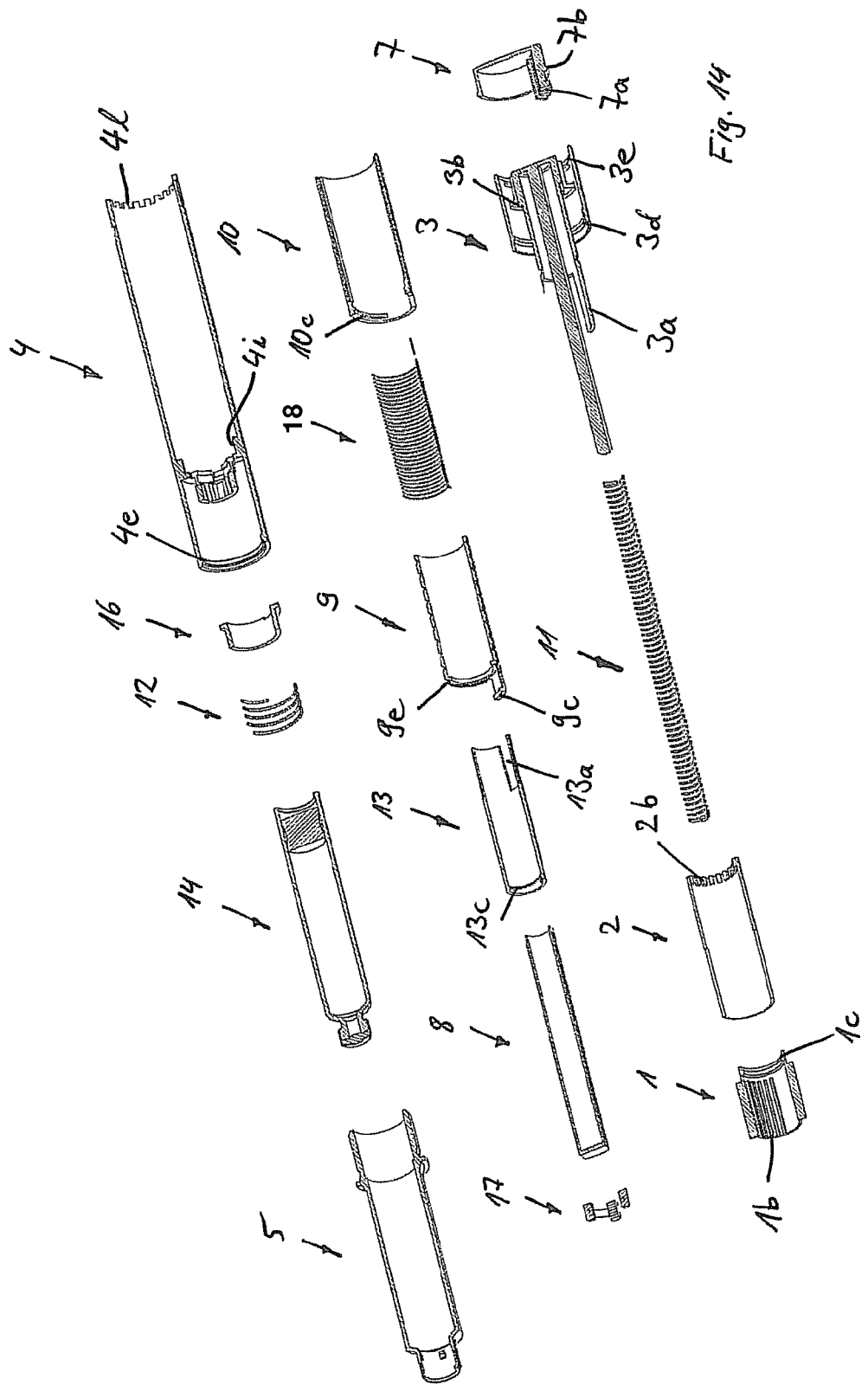

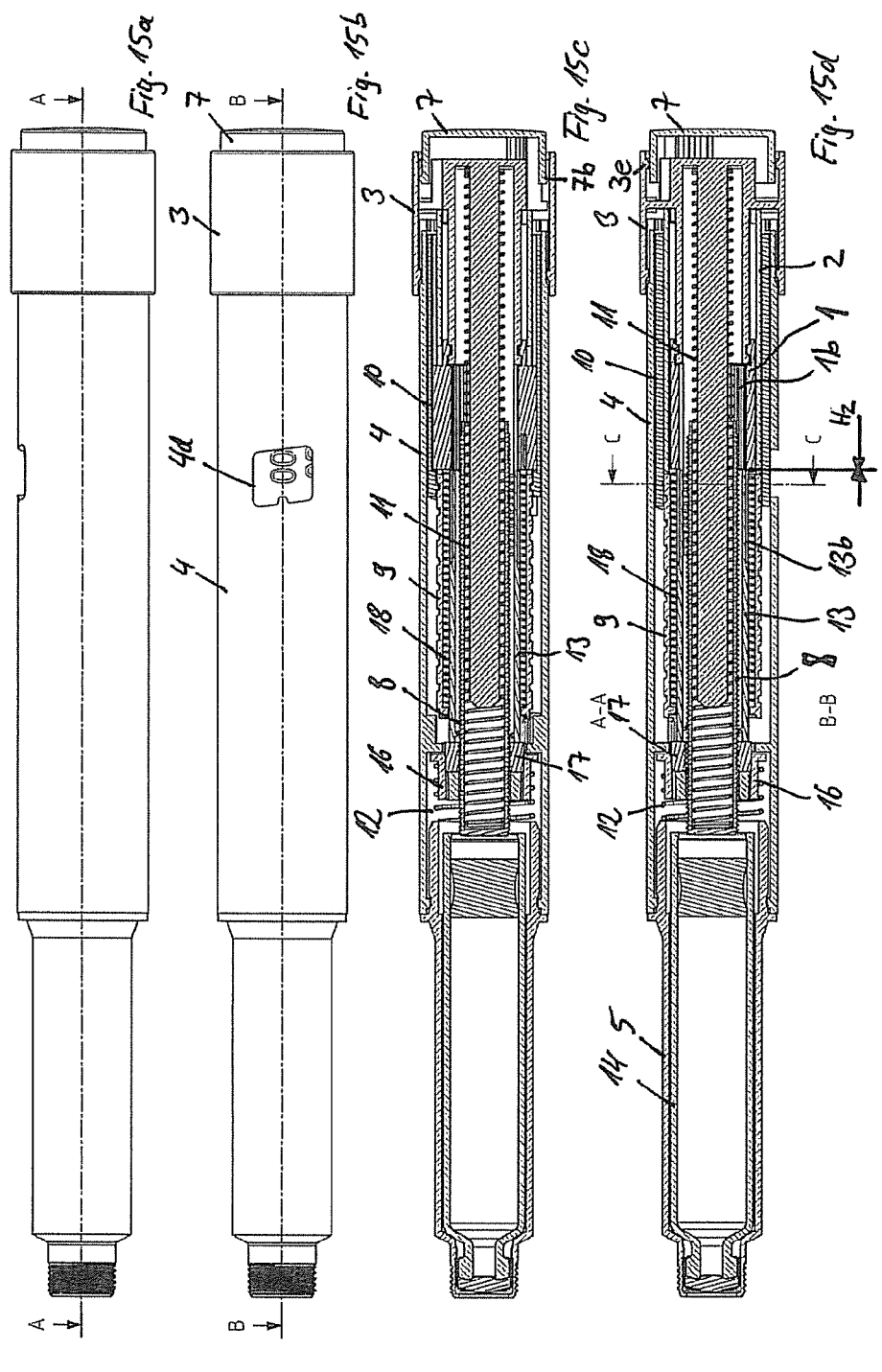

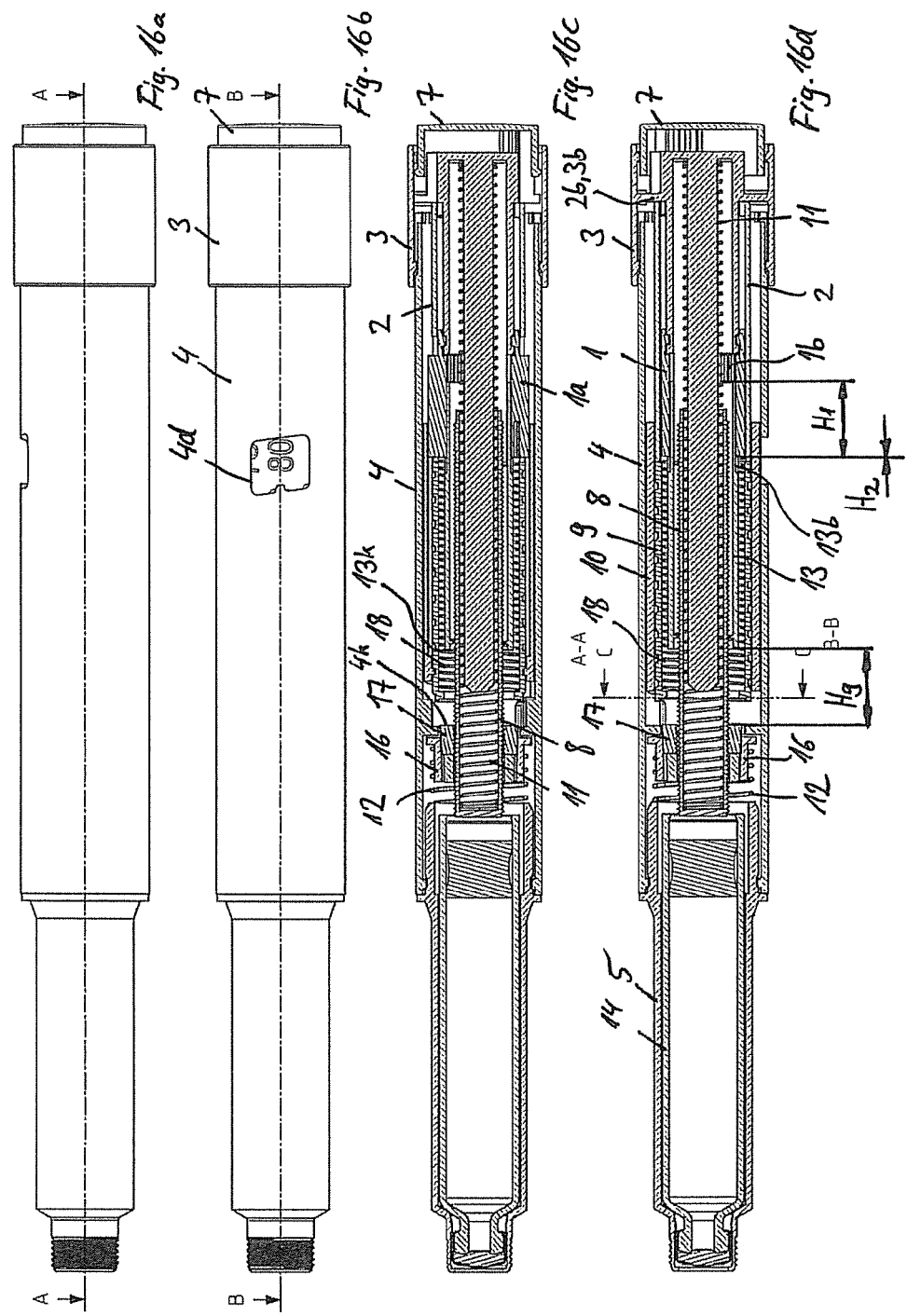

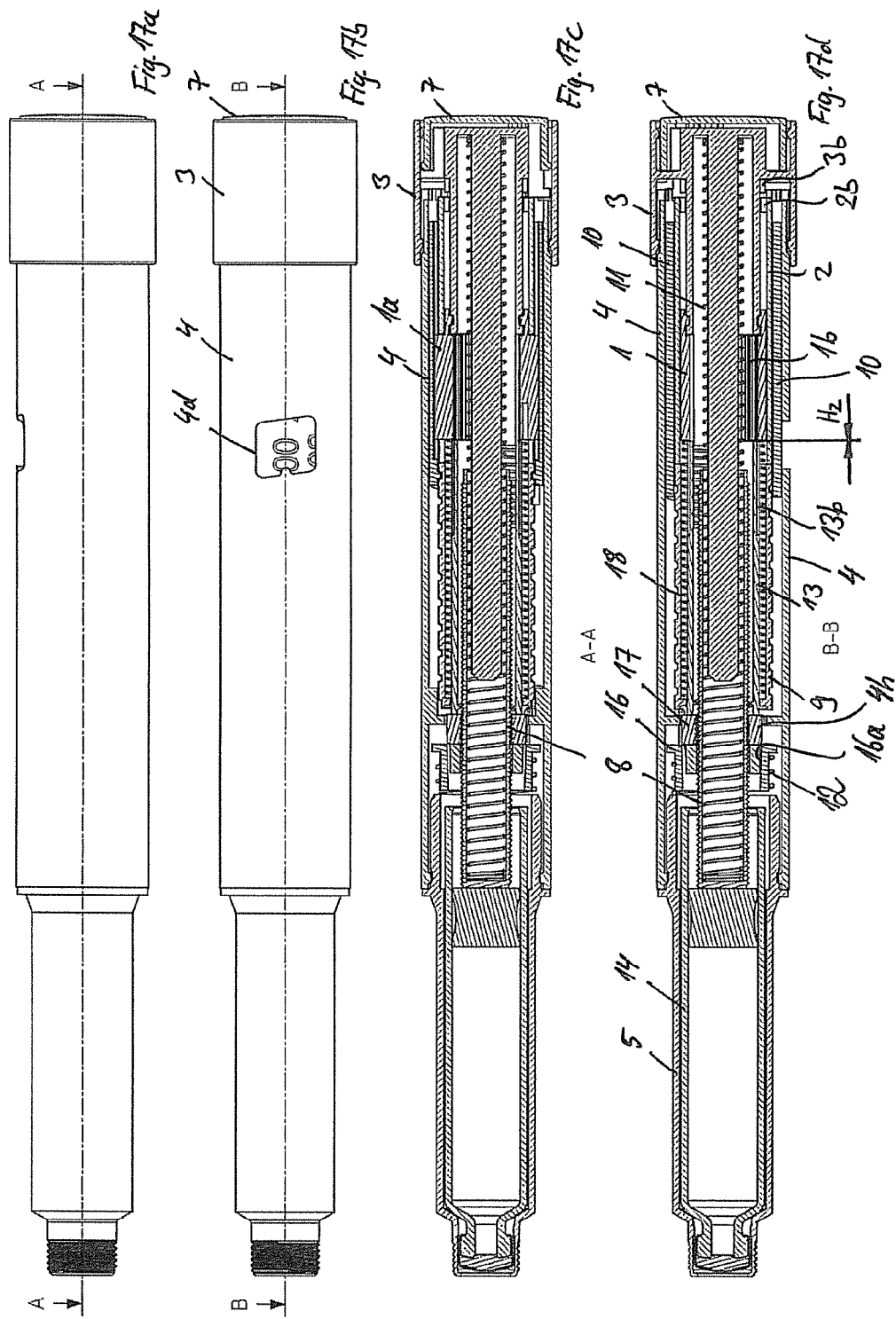

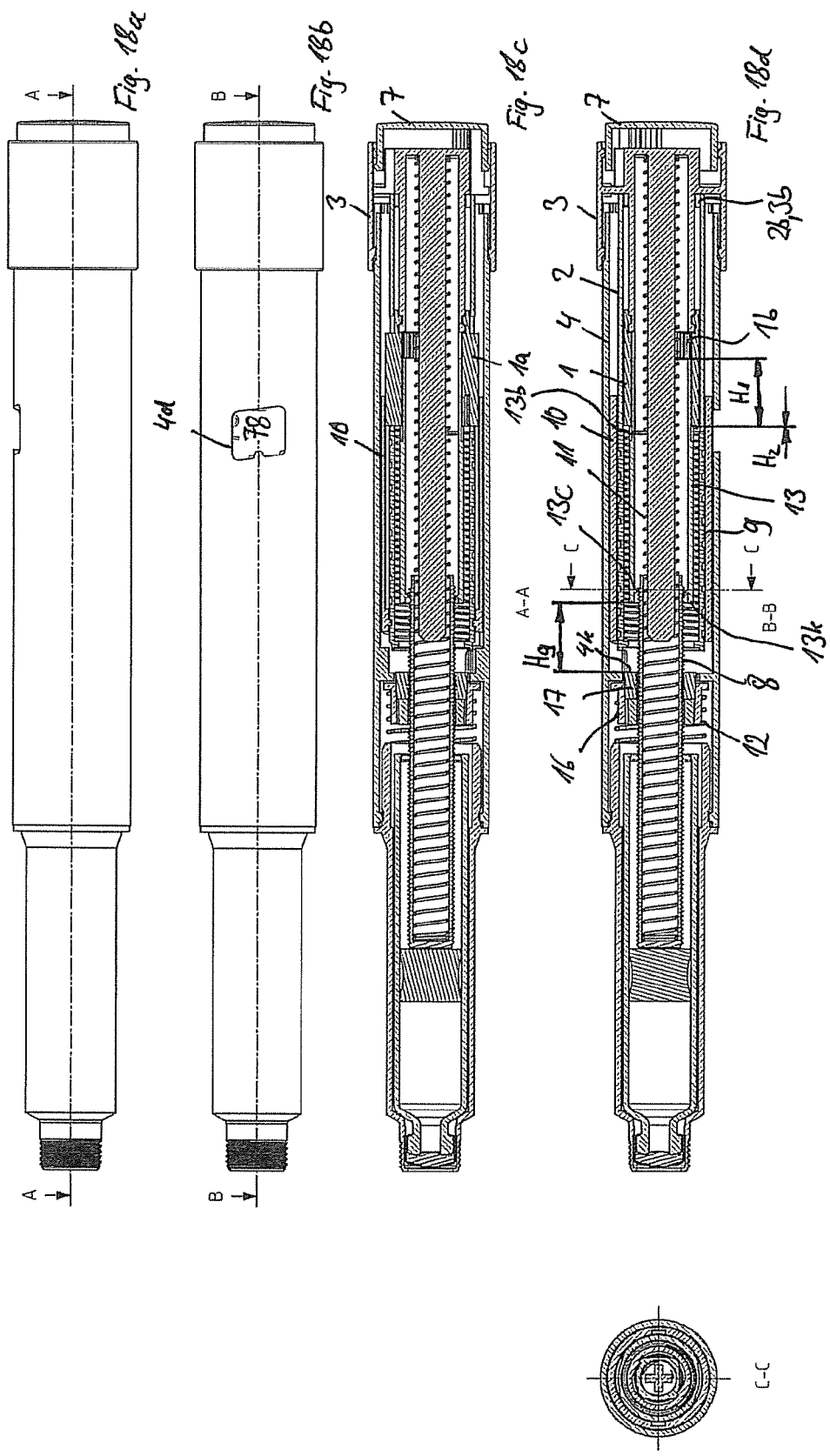

INJECTION DEVICE WITH DOSE DISPLAY FOR SIGNALING THE END OF THE INJECTION

CROSS-REFERENCE TO RELATED APPLICATIONS

This application is a Continuation of International Patent Application No. PCT/CH2013/000125 filed Jul. 11, 2013, which claims priority to European Patent Application No. 12 178 916.8 filed Aug. 1, 2012, the entire contents of each are incorporated herein by reference.

BACKGROUND

The invention relates to a drive and metering device for an injection device for administering a liquid product, particularly a medicine such as insulin. A product dose to be administered can be set with the drive and metering device and preferably can be discharged by means of multiple individual discharges, wherein the metering and discharging steps can be repeated multiple times. The invention thus also relates to an injection device having such a drive and metering device. In particular, the drive and metering device has a mechanically acting dose display, on which the dose to be administered can be read.

From the prior art, particularly WO 2009/105909A1, an injection device is known that has a housing in which a dose display sleeve is arranged. A metering button that can be rotated and is axially fixed relative to the housing is arranged at the rear end of the housing. By rotating the metering button, the dosage display drum is screwed along a thread formed by the housing. The set product dose can be read through a window of the housing. By actuating an actuating button, likewise at the rear end of the housing, a preloaded drive spring is released, which drives a piston rod for discharging the product and simultaneously turns back the dose display drum proportionally to the amount of discharged product, the dose values displayed in the window being counted down or running back in the direction of the zero-dose value.

In case of an interruption of the dose discharge, this device advantageously allows the amount of product yet to be discharged to be read in the window. The user of the injection device can recognize the end of product discharging in that the dose indicator stops and the value zero can be read in the window.

There are patients, however, who cannot securely perceive the signaling by the lack of a movement. Instead they require active signaling.

SUMMARY

One problem addressed herein is to specify a drive and metering device for an injection device that actively signals the user that discharging of the product is finished or nearly finished. The problem is solved with the drive and metering device as disclosed herein as well as disclosed advantageous refinements.

Disclosed implementations provide a drive mechanism, more particularly a drive and metering device, for an injection device for administering a liquid medicine or product. The drive and metering device advantageously has a housing. The housing is preferably sleeve-shaped and/or elongated in shape. The housing can extend along a longitudinal axis, for example.

The housing can optionally accommodate a product container or can itself constitute the product container. The housing can be in one or more parts. For example, the housing can form a proximal housing part that comprises or has the drive and metering device. The housing can additionally have a product container holder, which receives a product container such as a carpule and is connected to the housing or the proximal housing part. This connection can be such that the product container holder and the housing or the proximal housing part are non-detachable after connection, i.e., only detachable from one another by destroying connecting elements. Such a solution is particularly advantageous for single-use injection devices, which can be disposed of as a whole after the product contained in the product container has been completely discharged. Alternatively, the product container holder can also be detachably connected to the housing, whereby it may be possible to use the driving and metering device several times if necessary, i.e., to replace an empty product container with a filled product container.

The housing is principally used in order to be gripped by the user of the device. In particular, the housing can have a substantially cylindrical shape. The housing can have an indicating means, particularly a window, by means of which or through which the currently set dosage can be read, preferably from a scale of a dose-setting element.

The drive and metering device comprises a dose display element, over the circumference of which a dose scale is arranged. The dose display element can be annular in cross section, for example. The dose display element can be a dose display drum or a dose display ring, for example. The dose scale can extend over the circumference of the dose display element, preferably in a helical shape. The dose scale preferably comprises a plurality of dose values, which are arranged one after another and produce the dose scale. These are preferably numerical values that indicate the desired product dose in international units (IU).

Alternatively, the dose scale can be arranged without a pitch over the circumference of the dose display element, such as the dose display ring, in which case the scale values then repeat after a revolution of the dose display element. In a dose scale with a pitch, i.e., a helical dose scale, the dose display element, particularly the dose display drum, can be rotated more than one revolution without the scale values repeating, whereby higher or more scale values can advantageously be represented. The drive and metering device further comprises an indicating means, wherein the dose display element, in order to set the dose, can be rotated relative to the indicating means and particularly about a rotational axis that preferably corresponds to the longitudinal axis of the drive and metering device or/and the dose display element. This movement can be a purely rotational movement, i.e., a rotational movement without superimposed axial movement. Preferably an axial movement is superimposed on the rotational movement, whereby the dose display element is screwable relative to the indicating means in order to set the dose to be administered. A screwable dose display element can advantageously be combined with a helical dose scale, the screwing movement and the dose scale preferably having the same pitch. A dose display element without axial movement can be advantageously combined with a pitch-free dose scale.

A value of the dose scale that corresponds to the set dose can be read out by means of the indicating means, which is preferably formed on the housing. The indicating means can be a window, for example, which can be formed by an opening in the housing or by a transparent insert. Alternatively or optionally, the indicating means can be an arrow or have an arrow, which marks the value of the dose scale corresponding to the set dose in addition to the window. This is advantageous if a second value appears in the window, at least partially, in order to ensure an unambiguous choice of dose, for example. The pointer can be a protrusion or an imprint or a notch or the like.

The drive and metering device comprises a metering member, which can be formed as a metering knob, for example, and can optionally be referred to as a setting element. The metering member can preferably be gripped by the user (patient, physician, medical assistance personnel) of the drive and metering device and preferably constitutes an external, more particularly externally accessible, surface of the drive and metering device. To adjust the dose to be discharged or administered, the metering member is preferably gripped by the user and rotated relative to the housing, and in particular to the indicating means, about an axis of rotation, which preferably corresponds to the longitudinal axis of the drive and metering device. The metering member is preferably connected axially fixedly to the housing, more particularly secured against displacement along a longitudinal axis of the housing, which advantageously facilitates the intuitive handling of the device by the user, because the user needs only to carry out a rotational movement of the metering member to adjust the dose.

In particular, the dose display element can be secured against rotation at least during the dose-setting, but can be connected or coupled to the metering member so as to be axially displaceable. For intuitive operation, it is advantageous if, when the metering member is rotated by a given angle of rotation, the dose display element is rotated by the same angle of rotation.

In particular, the dose display element can be rotatable in order to adjust the dose to be administered by rotating the metering member relative to the indicating means about an axis of rotation from a starting position, which can be a zero-dose position, for example, in which the zero dose can be read in the indicating means. The dose value of the dose scale, which corresponds to the set dose, can be read by using the indicating means.

Rotating the metering member in a first direction relative to the indicating means can increase the dose. Rotating the metering member in a second direction opposite to the first direction can reduce or correct the set dose.

In particular, the dose display element can be rotated or screwed back and forth between a maximum-dose position and a zero-dose position (starting position) by rotating the metering member back and forth in the first and second rotational directions. In the zero-dose position, the dose value or the digit "0" can advantageously be readable in the indicating means. In the maximum-dose position, the maximum product dose that can be set with the drive and metering device can advantageously be readable. The dose display element can be blocked in the zero-dose position against rotation in the second rotational direction, namely the rotational direction that would cause a dose of less than zero to be set. In the zero position, the display element can preferably only be rotated in a direction of rotation that causes an increase of the dose. In the maximum-dose position, the dose display element is preferably blocked against rotation in the first rotational direction, namely the rotational direction that would cause an increase of the dose past the maximum settable dose. Preferably, the dose display element in the maximum-dose position can only be rotated in the second rotational direction, which causes a reduction of the product dose.

For example, the dose display element can have a stop that strikes against a mating stop in the zero-dose position and thus prevents rotation in the second rotational direction. The same or an additional stop on the dose display element can prevent rotation of the dose display element past the maximum-dose position. In particular, an additional mating stop, namely a maximum-dose mating stop, can be provided for this purpose. The other mating stop can accordingly be referred to as the zero-dose mating stop. Thus the dose display element can have a zero-dose stop for the zero-dose mating stop and/or a maximum-dose stop for the maximum-dose mating stop. The stop or the stops are preferably active in the circumferential direction and/or in the axial direction.

The drive and metering device further comprises a discharge spring and an advancement member, such as plunger or a piston rod, which acts on a piston of the product container, more particularly strikes the piston, in order to displace the piston into the product container to discharge the product.

The discharge spring can store the energy necessary for discharging the product and transfer it to the advancement member in order to discharge the product, whereby the advancement member is moved in the advancing direction by a total discharge stroke that is proportional to the set product dose. If a dose of 30 IU is set, for example, the total discharge stroke is the path on which the advancement member travels along the longitudinal axis and causes a discharge of 30 IU from the product container.

By repeated metering and discharging, the entire product quantity that can be discharged in the product container can be discharged with several total discharge strokes.

The discharge spring can be coupled to the metering member, for example, in such a manner that a rotation of the metering member in the first direction cocks the discharge spring during the dose-setting. The spring can then store the energy required for the set dose.

The spring can preferably already be preloaded with sufficient energy upon delivery of the drive and metering device that the energy suffices for several discharges of the product dose, in particular for multiple total discharge strokes. The energy contained in the cocked spring is preferably sufficient to discharge the entire dischargeable quantity of product in the product container with multiple total discharge strokes. In this alternative, the metering member can be decoupled from the spring during dose-setting, i.e., not coupled to the discharge spring, in such a manner that a rotation of the metering member cocks the spring. In this manner, the metering member can be rotated by the user to set the dose with considerably less force exertion.

The invention is distinguished in that the dose display element is rotatable relative to the indicating means, more particularly into its starting or zero position, only toward the end of the total discharge stroke of the advancement member, i.e., at or shortly before the end of the total discharge stroke. Thereby, the user is actively signaled at the end of the discharge that the discharge has ended or will end in a few moments.

The total discharge stroke can comprise a first partial discharge stroke, wherein the dose display element is non-rotatable relative to the indicating means during the first partial discharge stroke and is rotatable relative to the indicating means after the first partial discharge stroke. In particular, the drive and metering device can comprise a spring, in particular a display resetting spring, which rotates the dose display element back into its starting or zero-dose position. This spring can act as a compression spring or a torsion spring, for example. The spring can be cocked by rotation of the metering member in a first rotational direction and can be relaxed by rotating the metering member in the second rotational direction. During the first partial discharge stroke, the spring cannot relax, i.e., remains cocked, wherein the dose display element is rotationally stationary relative to the indicating means for the housing, and when the first partial discharge stroke has been finished, the dose display element rotates back into the zero position or starting position, more particularly during a second partial discharge stroke.

In particular, the total discharge stroke can comprise or consist of the first partial discharge stroke and a second partial discharge stroke. During the second partial discharge stroke, the dose display element is rotatable, more particularly screwable, relative to the indicating means or the housing. The second partial discharge stroke is preferably smaller than the first partial discharge stroke. In regard to length, the second discharge stroke is preferably fixed or specified in the design, while the first partial discharge stroke is variable and/or dependent on the set product dose.

For example, the second partial discharge stroke can be less than or equal to 5 IU, or preferably less than or equal to 2 or less than or equal to 1 IU. The fact that the second partial discharge stroke is relatively small, in particular only 1, 2 or a few IU in size, has the effect that the dose display element is only rotated back or screwed back into its dose position toward the end of the total discharge stroke. In particular, the end of the second partial discharge stroke is also the end of the total discharge stroke. The end of the first partial discharge stroke is preferably the beginning of the second partial discharge stroke.

In preferred embodiments, the drive and metering device can comprise a clutch, particularly a display reset clutch, which couples the indicating means or/and the housing rotationally fixedly to the dose display element during the first partial discharge stroke and decouples them rotationally during the second partial discharge stroke. The engaged clutch couples the indicating means or the housing rotationally fixedly to the dose display element, while the disengaged clutch rotationally decouples the indicating means and/or the housing from the dose display element. The disengaged clutch allows the dose display element to be rotatable relative to the indicating means or the housing, in particular by means of the display reset spring, in the direction of the initial or zero-dose position.

The clutch preferably has a first clutch structure, which is formed by a metering sleeve rotationally fixed and axially movable relative to the metering member, and a second clutch structure, which is formed by a rotationally fixed and axially movable rotation element that is connected to the dose display element for conjoint rotation and is movable axially. The first and second clutch structures are engaged secured against rotation during the first partial discharge stroke, the engagement being detached during the second partial discharge stroke.

The first clutch structure, in particular the metering sleeve, is preferably coupled to or engaged with the advancement member in such a manner that the first clutch structure, in particular the metering sleeve, is moved jointly with the advancement member by the first partial discharge stroke length and preferably also by the second partial discharge stroke length.

In particular, the clutch can be engaged, or the first clutch structure can be moved into the rotation-proof engagement with the second clutch structure, when the dose display element is moved out of its initial or zero-dose position by rotation of the metering member in the first rotational direction.

In particular, the clutch is disengaged when the dose display element is moved by rotation of the metering member in the second rotational direction into the initial or zero-dose position.

The metering sleeve preferably has an internal thread, which engages with an external thread of the advancement member and can be screwed by rotating the metering member relative to the advancement member. A metering distance between the metering member and a metering stop can be increased by rotating the metering member in the first rotational direction, which causes a dose increase. In particular, the metering distance between the metering stop and the metering sleeve can be reduced by rotating the metering member in the second rotational direction, which causes a dose reduction. The distance between the metering sleeve and the metering stop corresponds in particular to the total discharge stroke of the advancement member.

The metering stop is preferably a stop acting in the axial direction and can be formed, for example, by the housing or an element fixed relative to the housing such as a housing insert that is connected non-rotatably and axially fixedly to the housing and therefore can be considered part of the housing.

The first clutch structure and the second clutch structure can each have respective toothing running over the circumference, the first clutch structure preferably having external toothing and the second clutch structure preferably having internal toothing, or vice versa.

The first clutch structure is preferably movable relative to the second clutch structure along the longitudinal axis of the drive and metering device when the clutch is engaged.

The rotation element is preferably rotatable and axially fixed relative to the metering member and/or the housing and/or the indicating means. In particular, the rotation element is engaged rotatably and axially fixedly with the metering member or the housing.

The discharge spring can be a spring, particularly a coil spring, acting as a compression spring. Alternatively, the discharge spring can be a spring such as a coil spring or a spiral spring that acts as a torsion spring.

The discharge spring, preferably acting as a compression spring, can be cocked under pressure and can act on the advancement member, and can, in particular, be supported on the advancement member and the housing or on an element, such as the metering member, that is connected at least axially fixedly to the housing. For example, the advancement member can be sleeve-shaped, wherein the discharge spring can be arranged at least partially inside the sleeve-shaped advancement member. The discharge spring can be supported at the distal end thereof on the advancement member, particularly on a shoulder projecting inward, e.g., at the distal end of the advancement member, and can be supported at the proximal end on the housing or the element connected at least axially fixedly to the housing.

The advancement member is preferably rotationally fixed relative to the housing or the indicating means and movable axially along the longitudinal axis, more particularly engaged secured against rotation and movable axially. For example, the advancement member can have a longitudinal guide such as a longitudinal groove, with which the housing or an element fixed relative to the housing engages and guides the advancement member secured against rotation and movably along the longitudinal axis.

The driving and metering member can further comprise a gripping device, which holds the advancement member fixed axially, wherein the engagement of the gripping device is detachable such that the advancement member is movable relative to the gripping device along the longitudinal axis of the drive and metering device. The gripping device can engage with an external thread or toothing of the advancement member, for example, which is rotationally fixed relative to the housing but movable axially, the gripping device securing or blocking the advancement member against movement along the longitudinal axis, particularly in the distal direction. The engagement of the gripping device with the advancement member can be detachable, by actuating an actuating element for example, whereby the advancement member can be displaced in the distal direction or discharge direction, more particularly by means of the cocked discharge spring.

For example, the gripping device can have, in particular, a resiliently arranged gripping engagement member, which engages with the advancement member, more particularly with the external thread or toothing thereof. The resiliently arranged retaining engagement member can be preloaded in such manner that it is moved by the preloading out of engagement with the advancement member. For example, the retaining engagement member can be formed by the housing or an element fixed relative to the housing or by a gripping ring, wherein the housing or the element fixed relative to the housing, or the gripping ring, effects the resilient arrangement of the retaining engagement member.

The gripping device can further comprise a clamping piece, more particularly a clamping sleeve, which can be moved back and forth relative to the retaining engagement member along the longitudinal axis between a clamping position and a release position, wherein the clamping piece presses the retaining engagement member into engagement with the advancement member when the clamping piece is in the clamping position and releases the retaining engagement member when the clamping piece is in the release position, such that the retaining engagement member can be moved out of the engagement with the advancement member that secures the axial movement. For example, the gripping device can be a spring acting on the clamping piece, in particular a spring acting as a compression spring that holds the clamping piece in the clamping position. By actuating the actuating element, the clamping piece can be displaced by cocking the spring, which can also be referred to as the clamping piece reset spring, whereby the retaining engagement member is released. The clamping piece preferably has a surface inclined relative to the longitudinal axis, more particularly at an acute angle or conically, which slides along the retaining engagement member. If the actuating element is no longer being actuated, the clamping piece reset spring presses the clamping piece back into the retaining position.

In preferred embodiments, the drive and metering device further comprises a bearing element, with which the dose display element is engaged. This engagement advantageously effects the rotational and/or screwing movement of the dose display element relative to the indicating means. For example, the engagement between the dose display element and the bearing element can be a threaded engagement. In particular, the bearing element can have an external thread and the dose display element an internal thread, these threads engaging with one another and thereby causing the dose display element to be screwable relative to the bearing element. Alternatively, the dose display element can be in an axially fixed and rotatable engagement with the bearing element, which is particularly advantageous for a dose display ring.

The bearing element is preferably rotationally fixed and axially movable relative to the housing. In particular, the bearing element can engage with the housing in a rotationally fixed manner and be movable axially. For example, the housing can have a longitudinal groove with which the bearing element engages. The bearing element is preferably movable, more particularly by the actuation of an actuating element, in the distal direction against the force of a reset spring, acting in particular as a compression spring. The reset spring can reset the bearing element in the proximal direction, in particular by resetting the actuating element. The reset spring for the bearing element can additionally take on the task of the clamping piece reset spring, so that the reset spring has at least a double function.

The bearing element can be connected axially fixedly to the clamping piece or can form the clamping piece. This has the effect that the clamping piece can be displaced together with the bearing element along the longitudinal axis. In particular, the dose display element can be displaced together with the bearing element in addition to a possible screwing movement.

The drive and metering device can have a clutch element, for example, which is connected by means of a clutch, particularly a detachable metering clutch, for conjoint rotation with the metering member. To set the dose, the metering member is connected, secured against rotation, to the clutch element, i.e., the clutch is engaged, the clutch being opened for discharging the set dose, so that the clutch element can be rotated relative to the metering member. The clutch element can have a third clutch structure such as toothing, more particularly external toothing, extending over the circumference. The metering member can have a fourth clutch structure such as toothing, more particularly internal toothing, extending over the circumference. If the clutch is engaged, the third clutch structure is in a rotationally fixed engagement with the fourth clutch structure, the third clutch structure being disengaged from the fourth clutch structure when the clutch is disengaged. The clutch is preferably pushed by a clutch spring into an engaged position. The clutch spring can be a coil spring acting as a compression spring, for example. The task of the clutch spring can be taken over by the reset spring, for example, so that the reset spring holds the clutch element in the rotationally fixed engagement with the metering member. The clutch can preferably be disengaged by actuating an actuating element, in particular against the force of the clutch spring. The clutch element can engage with the bearing element, for example, such that it displaces the bearing element in the distal direction by actuation of the actuating element.

The clutch element can preferably be connected permanently rotationally fixedly and movable axially to the dose display element and/or the rotation element. Via the engagement formed between the metering member and the clutch element, the dose display element and/or the rotation element can be coupled to the metering member for conjoint rotation, wherein the rotationally fixed coupling can be released by disengaging the clutch.

For example, the driving and metering member can comprise an actuating element that can be actuated, more particularly pressed, by the user of the drive and metering device in order to discharge the product. The actuating element can be formed as an actuating button. The actuating element can form an outer surface of the driving and metering device and/or can be accessible from the outside.

The actuating element can be formed on the proximal end, in particular the rear end, of the drive and metering device or can constitute this end. In this manner, the actuating element can advantageously be actuated, particularly pressed, with the thumb of the hand that is gripping the housing. The actuation can be ended by releasing the actuating element. "Actuating" is understood to mean the displacement of the actuating element into the driving and metering device, more particularly in the distal direction, which can effect the discharging of a product. The actuating element is advantageously displaceable relative to the metering element and in particular can be received by the metering element so as to be displaceable axially. The dose display element is preferably moved or even screwed at least axially relative to the actuating member during dose setting. In particular, the dose display element is movable axially relative to the actuating element by rotation of the metering member in the first or second direction. The actuating element is preferably coupled to the gripping device, more particularly the clamping piece, in such a manner that actuation of the actuating element causes the engagement of the actuation device, more particularly the retaining engagement element, with the advancement member to be released, whereby the advancement member is moved in the discharge direction. In particular, actuation of the actuating element causes a displacement of the clamping piece into the release position.

Alternatively or additionally, actuation of the actuating element has the effect that the bearing element is displaced together with the dose display element along the longitudinal axis relative to the indicating means. The fact that the bearing element has been displaced together with the dose display element can advantageously be read out on the indicating means and/or the dose display element. In this way, the user can monitor the operating status of the driving and display device, i.e., whether the driving and display device, and in particular the actuating element, is or is not actuated for discharging. In one variant, the dose display element can have a marking in addition to the dose scale, the marking being visible only if the actuating member has been actuated or the bearing element is displaced in the direction toward the indicating means.

The actuating element is preferably actuable against the force of a reset spring, in particular the reset spring that resets the bearing element and/or the clamping piece and/or the clutch element, wherein the reset spring can reset the unactuated actuating member to the unactuated position.

Alternatively or additionally, actuation of the actuating member causes the metering sleeve to be moved toward the metering stop, namely, by releasing the advancement member, such that the drive spring moves the advancement member together with the metering sleeve toward the metering stop. In other words, actuation of the actuating element releases the advancement member for movement thereof in the advancing, i.e., distal, direction.

In particularly preferred embodiments, the actuating member automatically remains in the pressed, i.e., actuated, position until the product discharge is finished, or until the dose display element has rotated back into the starting or zero-dose position, at least partially, but more particularly to a large extent or completely. That is to say, the actuating member remains in the actuated position even if the user is no longer pressing the actuating element. This advantageously ensures that, once the product discharge has been initiated, the set product dose is completely administered.

In particular, the actuating element can interlock with the metering member when actuated, wherein the interlocking connection can be released by means of the dose display element, particularly when it is rotating back. For this purpose, the actuating member can have at least one latching element, which interlocks with the metering member and is detached from the interlocking connection by the dose display element.

BRIEF DESCRIPTION OF THE DRAWINGS

FIG. 14 shows the representation from FIG. 13, with the individual parts represented in section.

FIGS. 15a-15d show various views of an injection device composed of the individual parts from FIGS. 13 and 14 in an initial or delivery state.

FIGS. 16a-16d show the views of the device from FIGS. 15a-15d, with a maximum set product dose.

FIGS. 17a-17d show the views of the device from FIGS. 15a-15d, after discharge of the set product dose.

FIGS. 18a-18d show the views of the device from FIGS. 15a-15d, in a state in which the dischargeable product dose contained in the product container is less than the maximum dose that can be set with the device.

DETAILED DESCRIPTION

Figure 1:
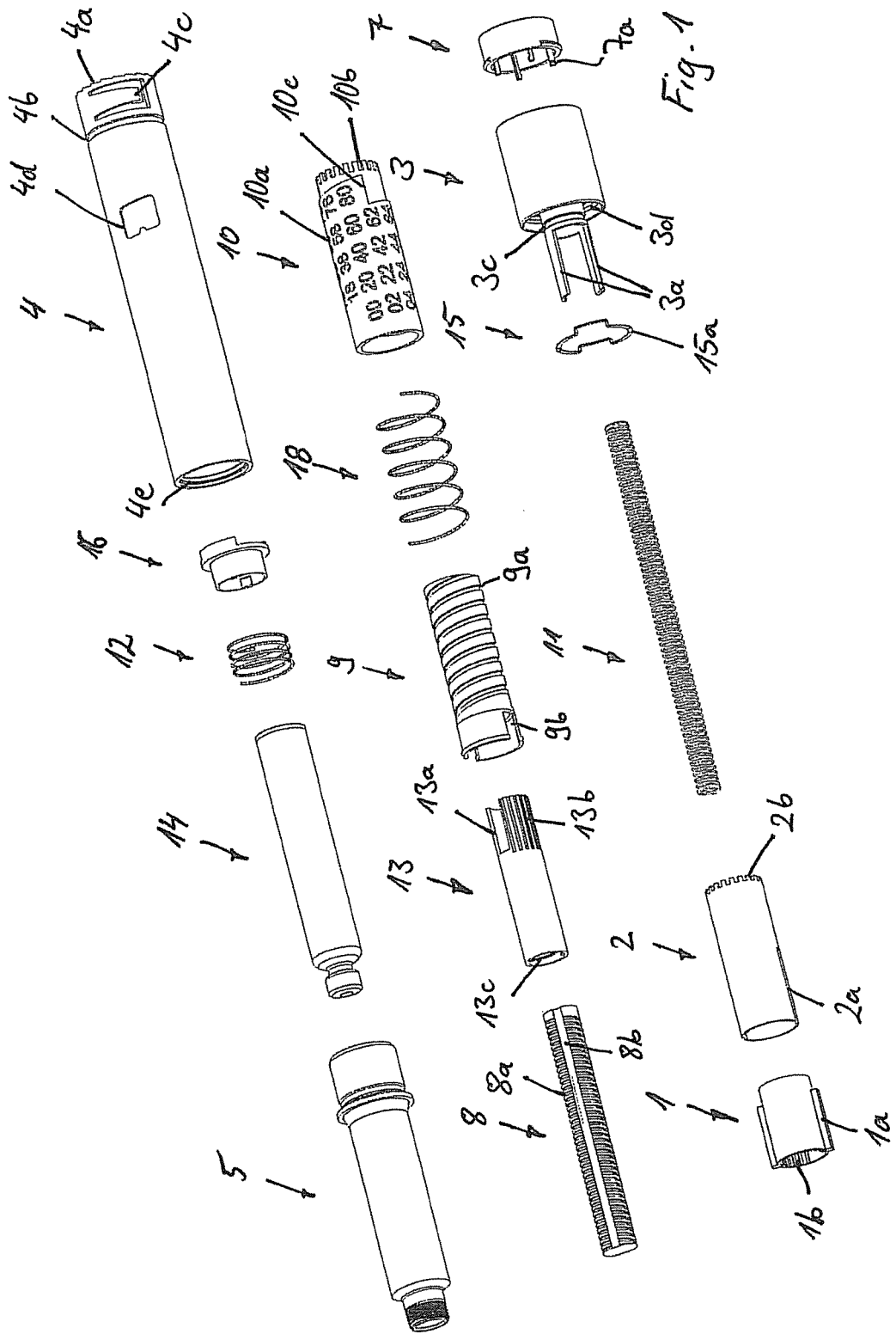
FIG. 1 shows an exploded view of an injection device having a drive and metering device according to a first embodiment.
Figure 2:
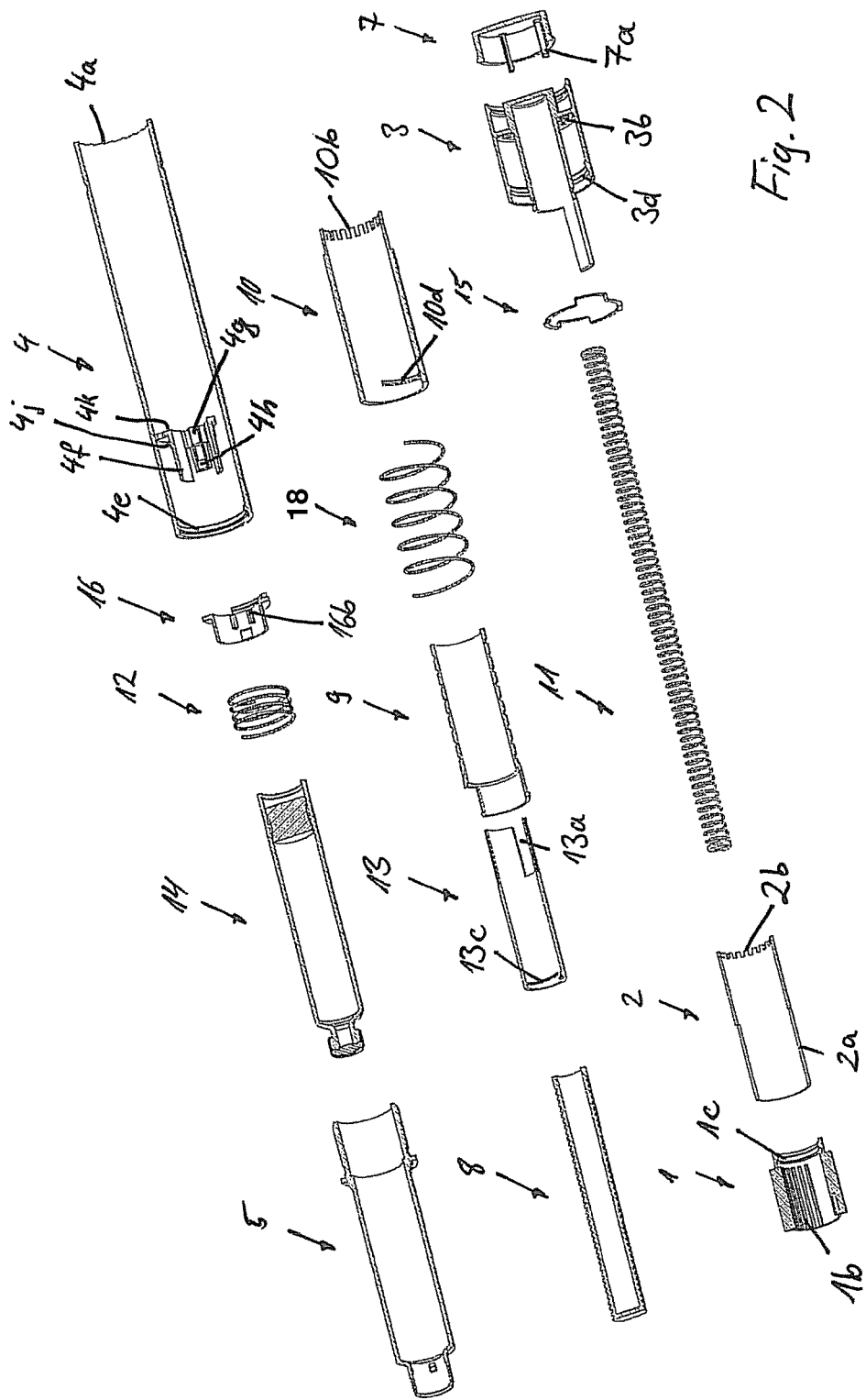
FIG. 2 shows the representation from FIG. 1, with the individual parts represented in section.
Figure 3:
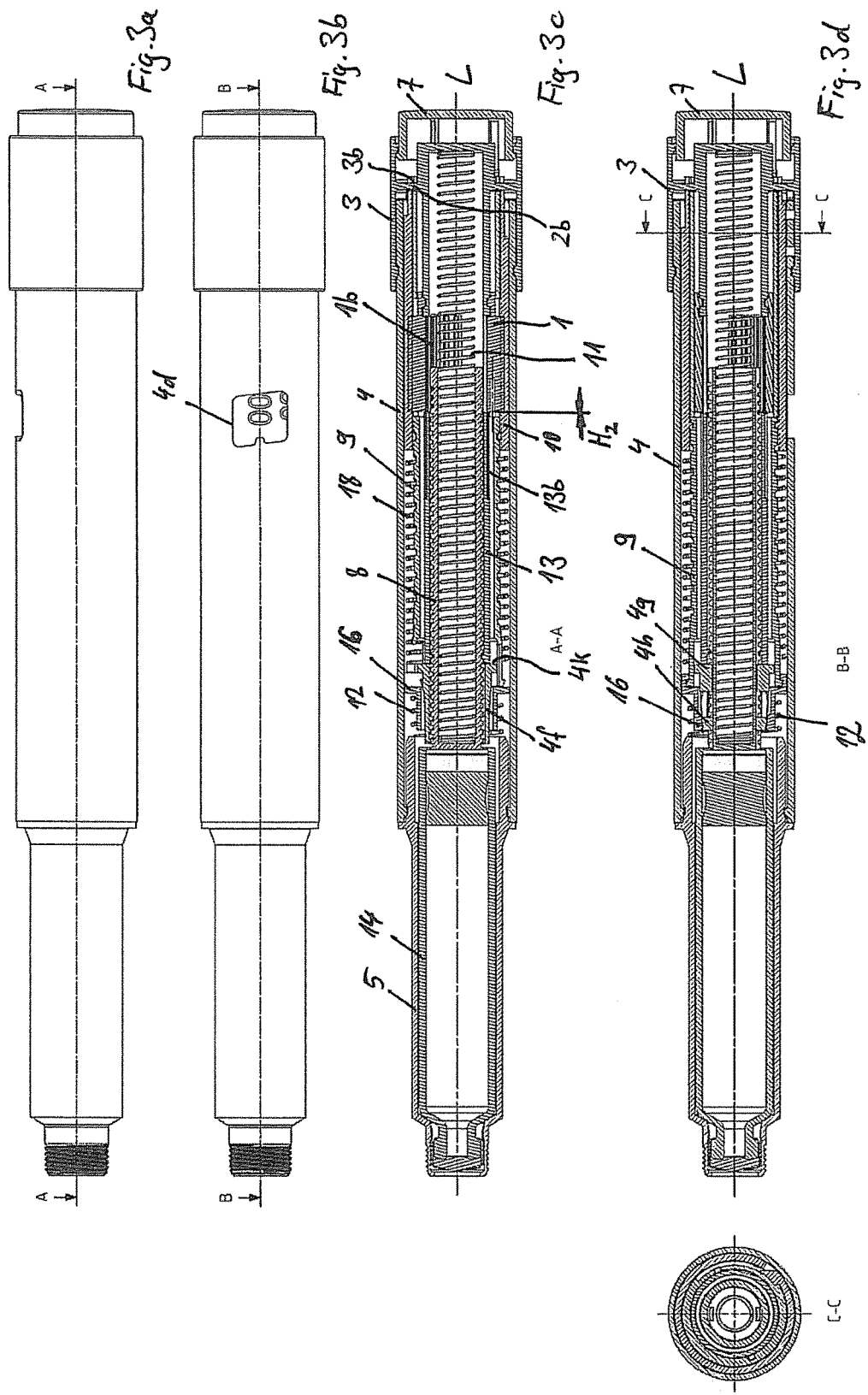
FIGS. 3a-3d show various views of an injection device composed of the individual parts from FIGS. 1 and 2, in an initial or delivery state.
Figure 4:
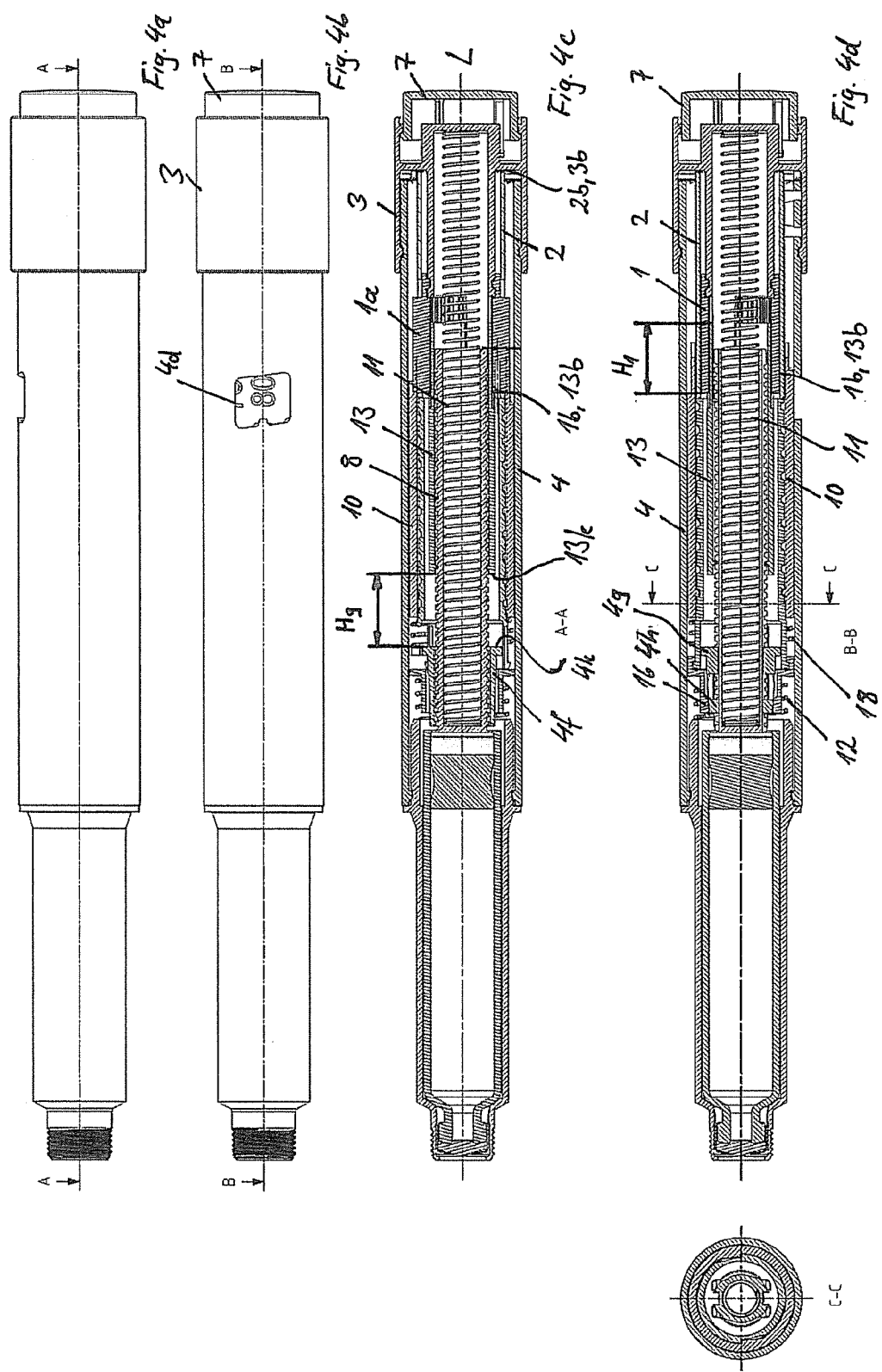
FIGS. 4a-4d show the views of the device from FIGS. 3a-3d, with a maximum set product dose.
Figure 5:
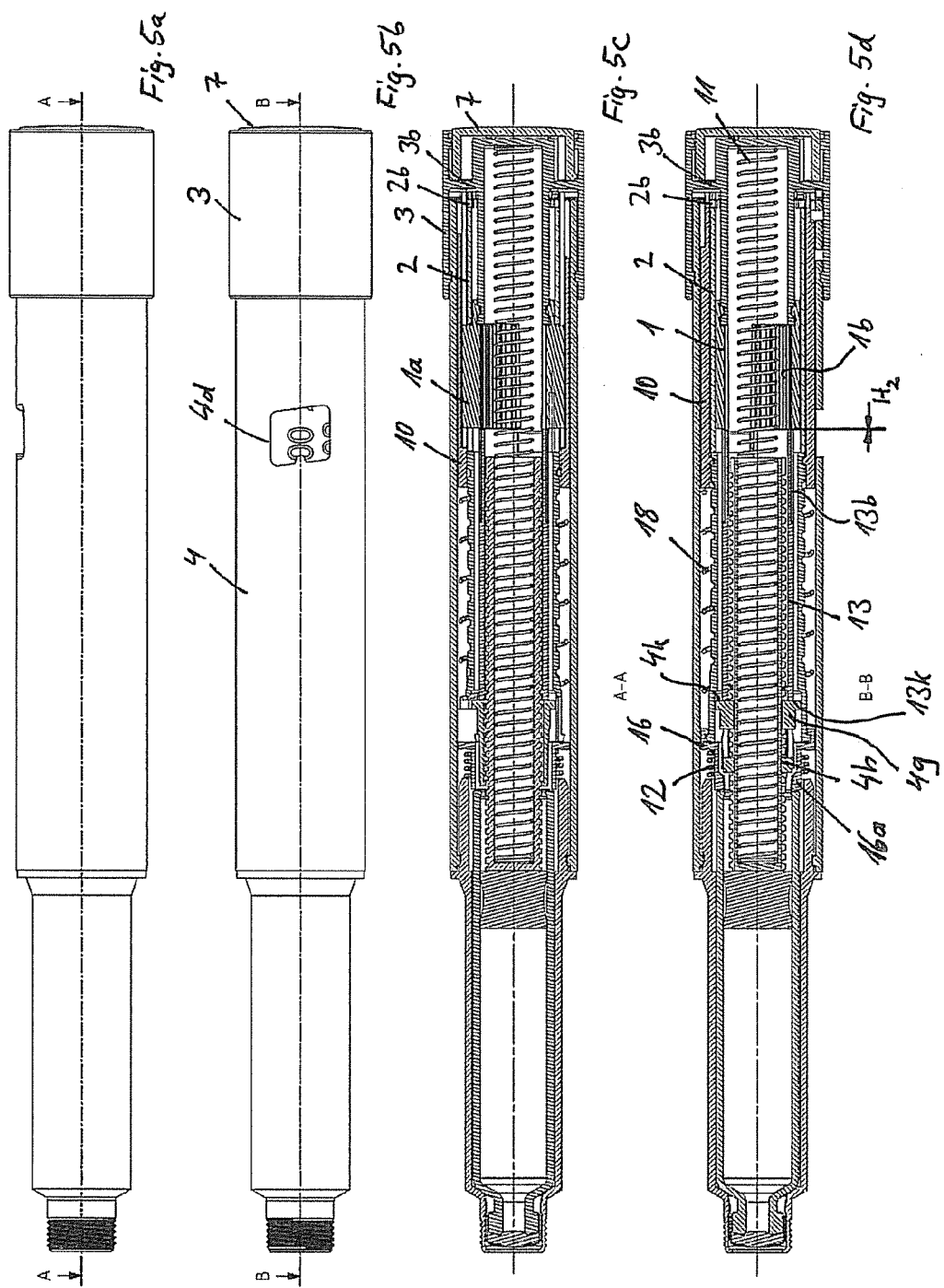
FIGS. 5a-5d show the views of the device from FIGS. 3a-3d, after discharge of the set product dose.
Figure 6:
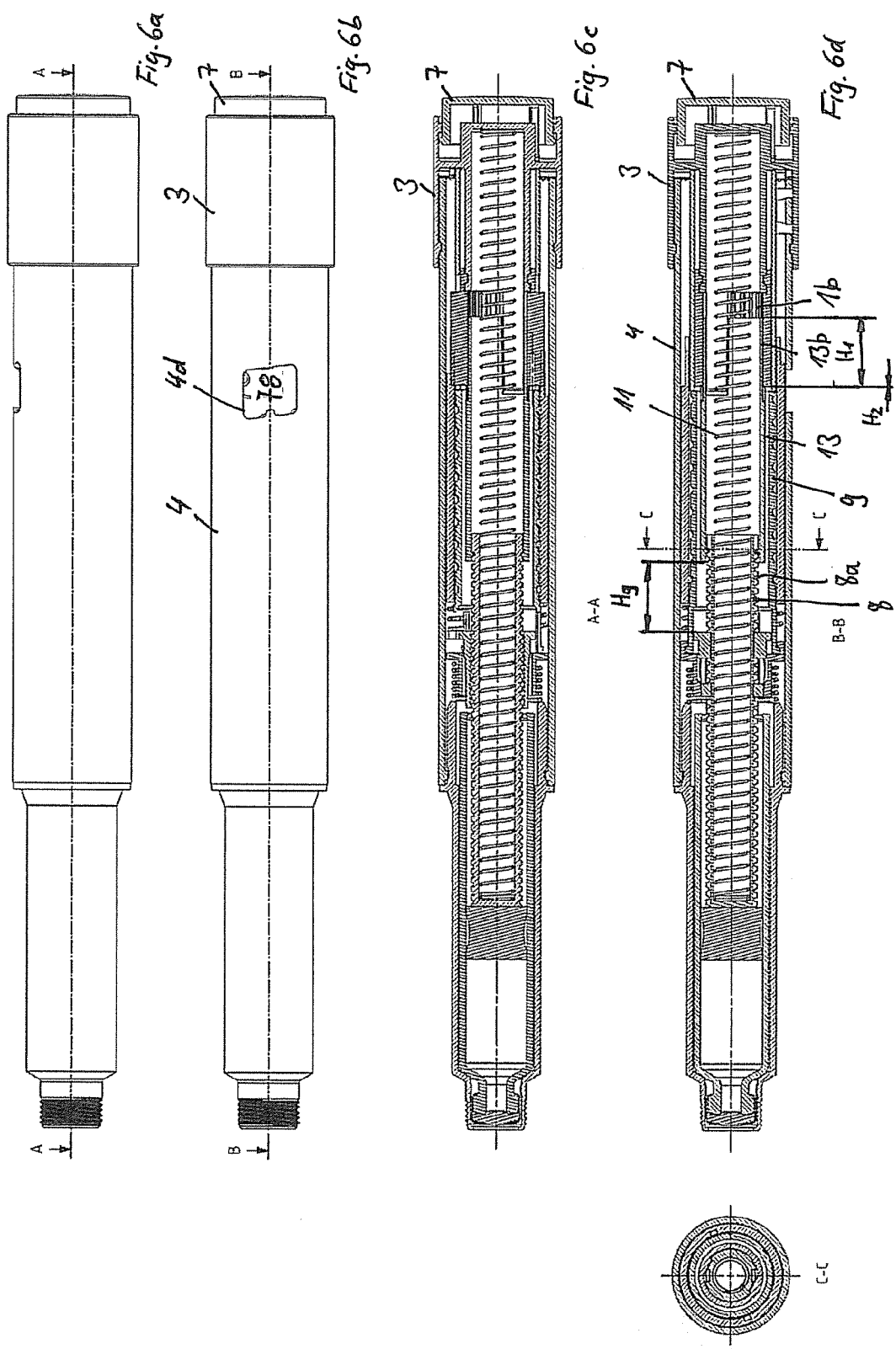
FIGS. 6a-6d show the views of the device from FIGS. 3a-3d, in a state in which the dischargeable product dose contained in the product container is less than the maximum dose that can be set with the device.
Figure 7:
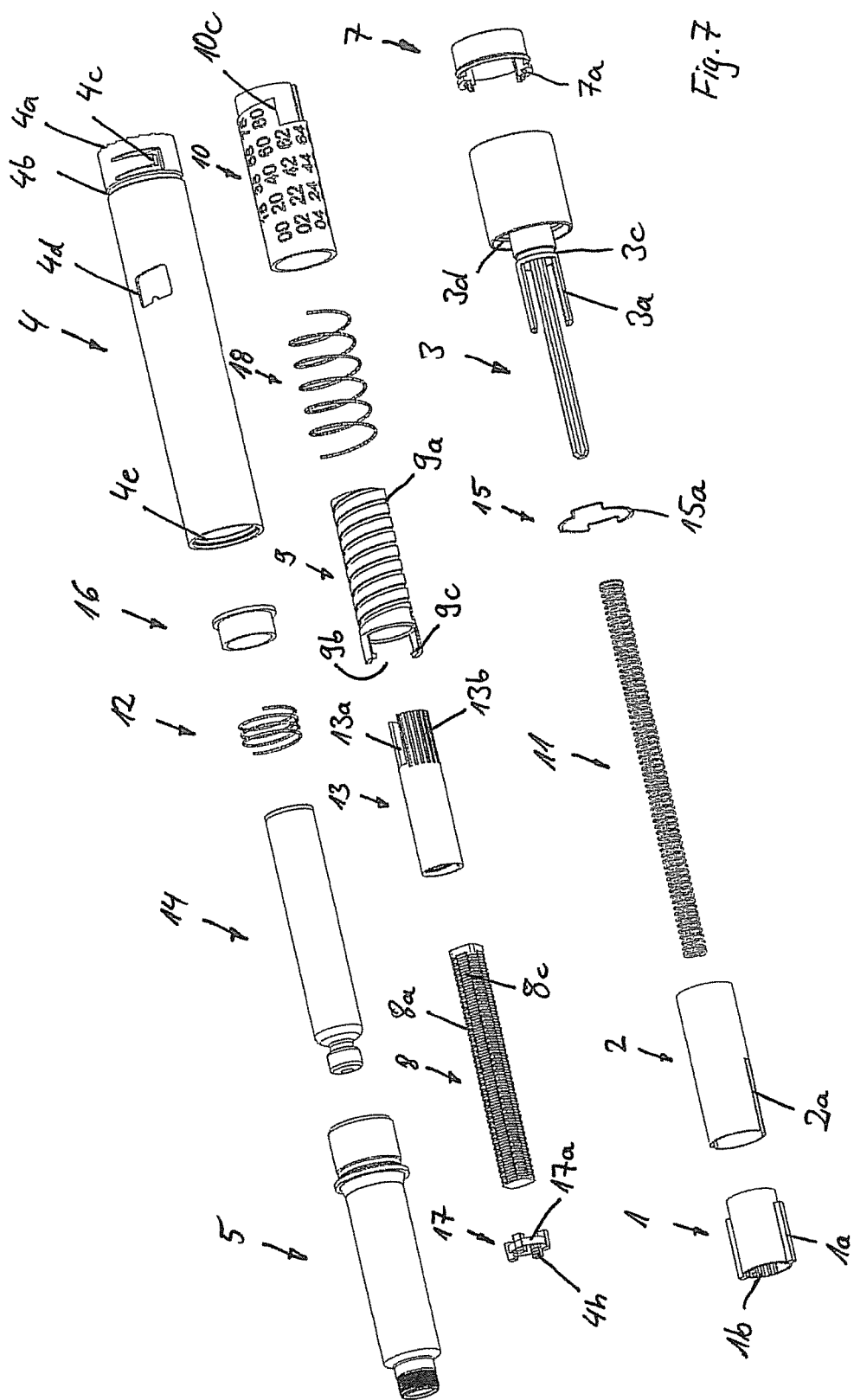
FIG. 7 shows an exploded view of an injection device having a drive and metering device according to a second embodiment.
Figure 8:
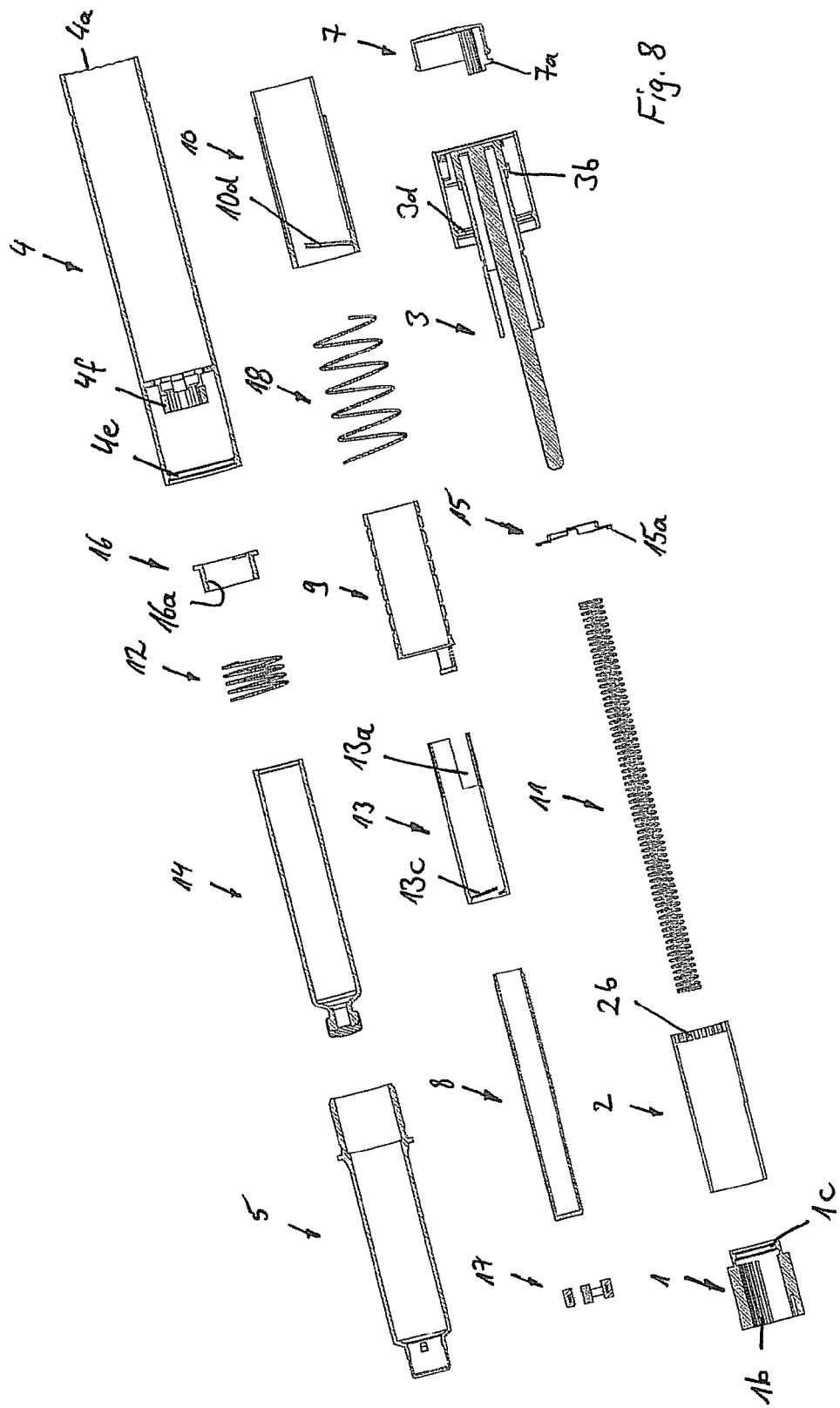
FIG. 8 shows the representation from FIG. 7, with the individual parts represented in section.
Figure 9:
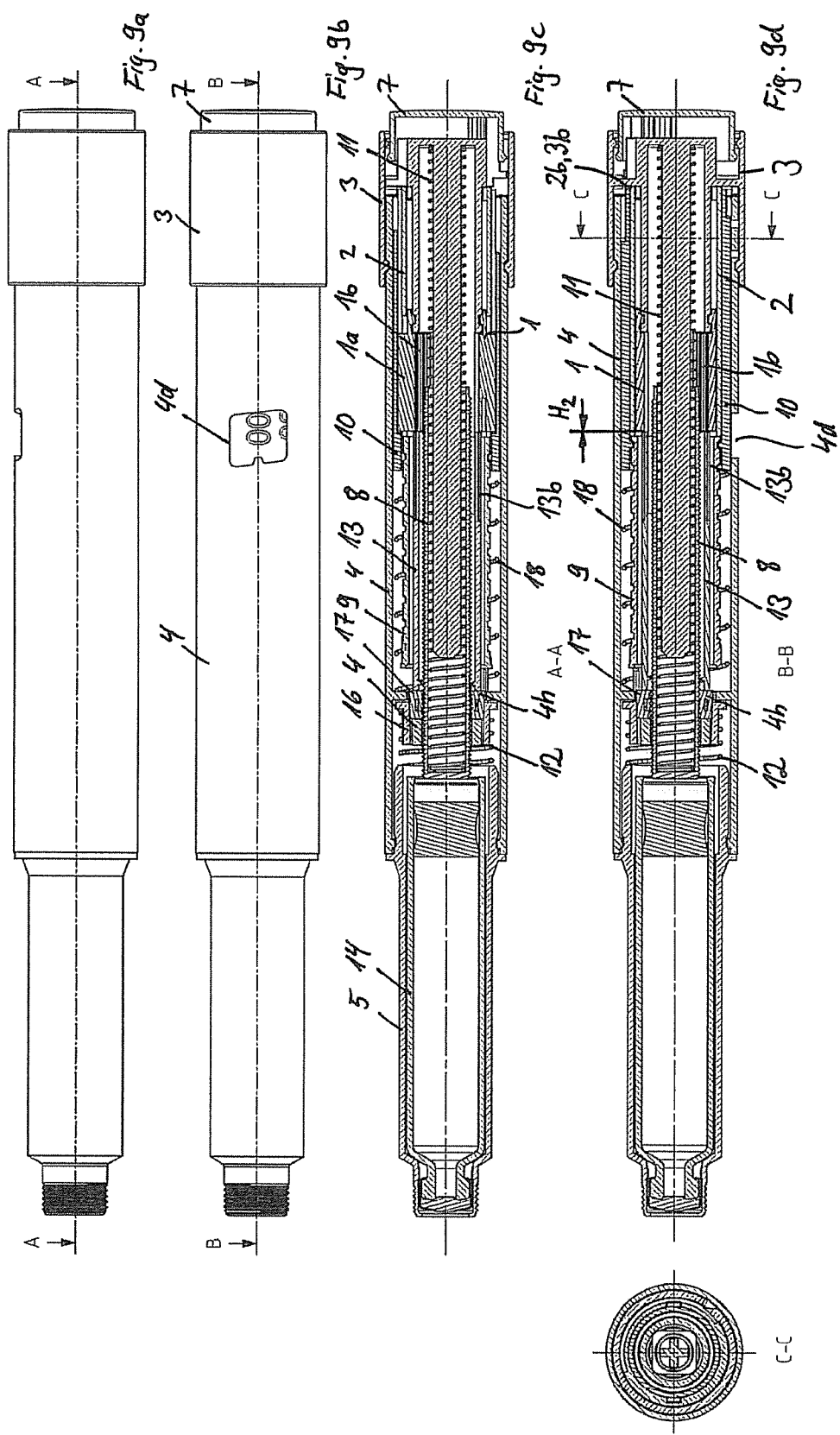
FIGS. 9a-9d show various views of an injection device composed of the individual parts from FIGS. 7 and 8 in an initial or delivery state.
Figure 10:
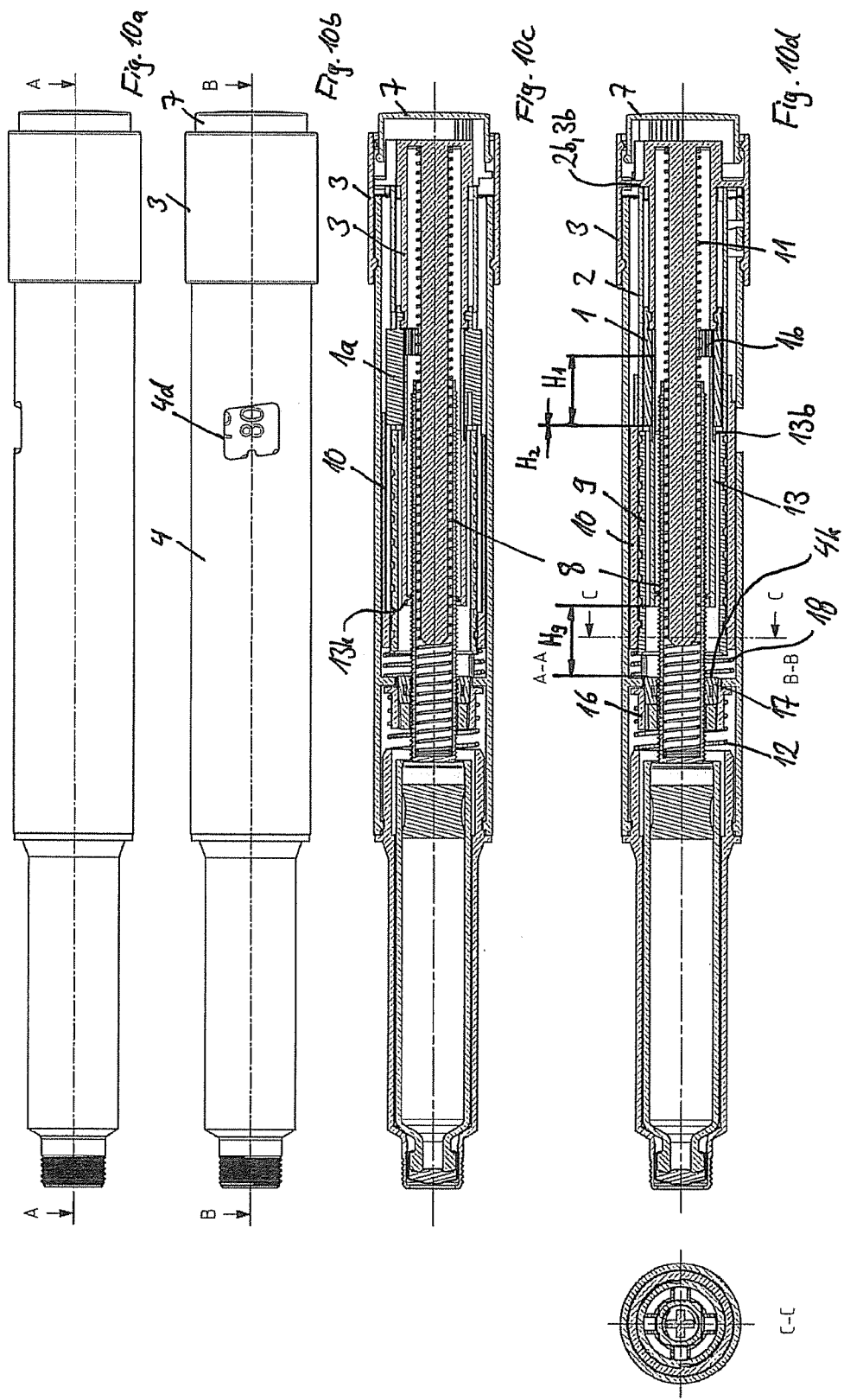
FIGS. 10a-10d show the views of the device from FIGS. 9a-9d, with a maximum set product dose.
Figure 11:
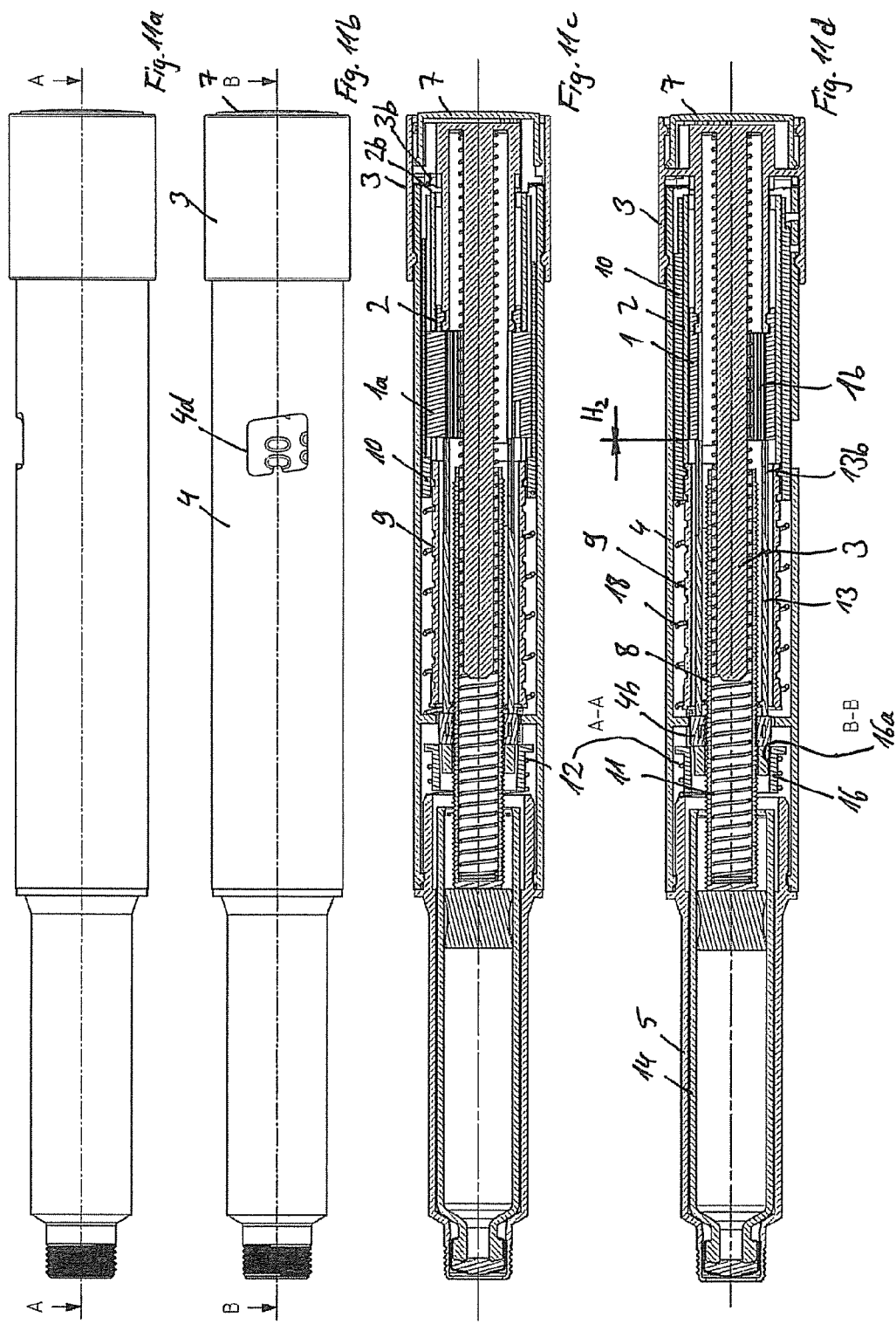
FIGS. 11a-11d show the views of the device from FIGS. 9a-9d, after discharge of the set product dose.
Figure 12:
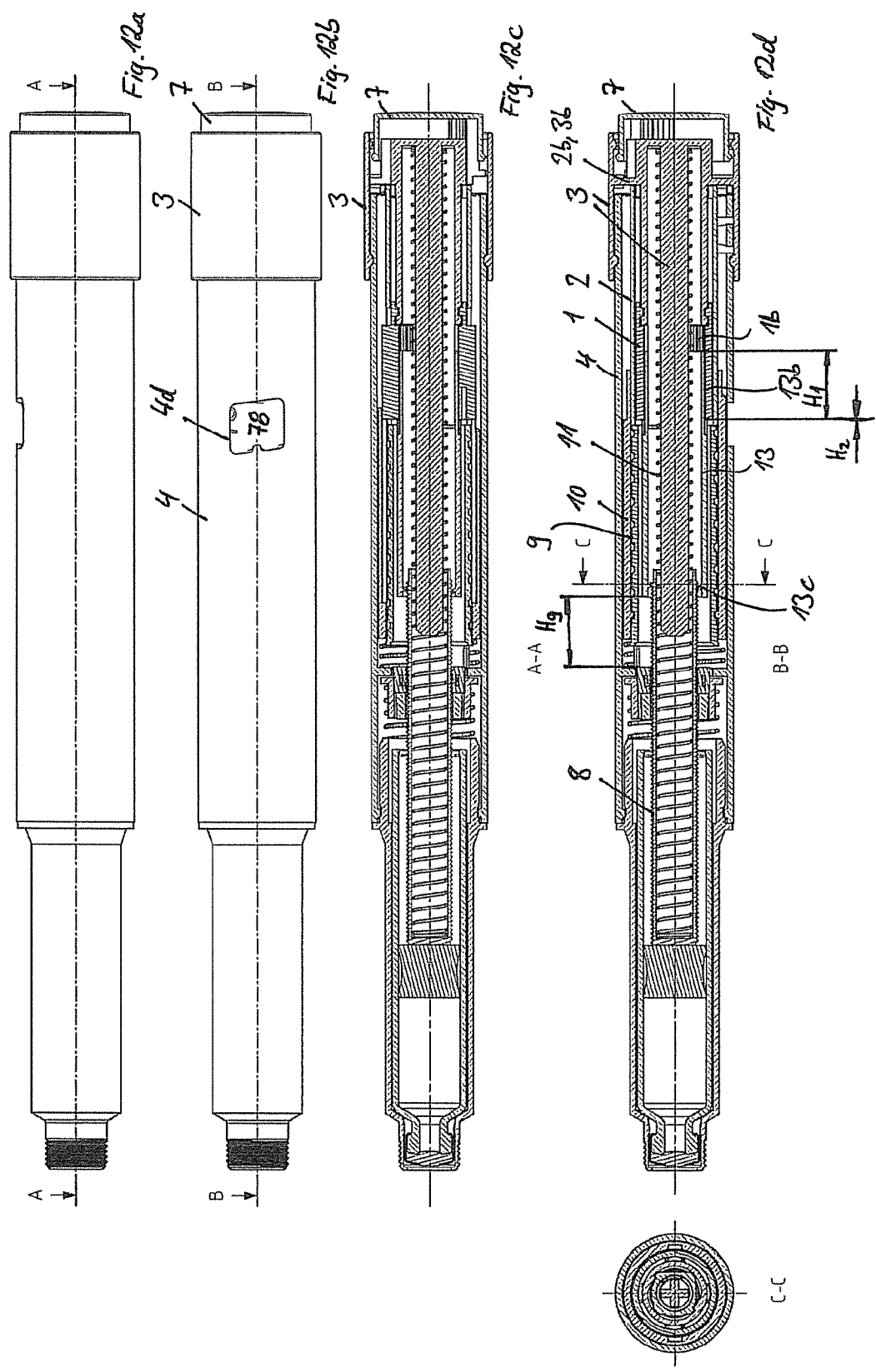
FIGS. 12a-12d show the views of the device from FIGS. 9a-9d, in a state in which the dischargeable product dose contained in the product container is less than the maximum dose that can be set with the device.

The first embodiment will be described first, with reference to FIGS. 1-6d. The second and third embodiments are similar to the first embodiment. To avoid repetition, only the features of the second and third embodiments that differentiate them from the first embodiment will be described. Identical reference numbers designate functionally and/or structurally identical components.

The drive and metering device has a sleeve-like housing 4, in which a window-like opening for forming an indicating means 4d is arranged. At the distal, i.e., front, end of the housing 4, a product container holder 5 is mounted, preferably non-detachably, more particularly snapped in, which holds a product container 14 in the form of a carpule. The carpule has a cylindrical housing, in which a piston is displaceably arranged. At the distal end, the carpule has a septum that can be punctured by a needle. The product to be administered is located between the septum and the piston. The product is forced out of the product container 14 by displacing the piston in the direction of the septum. A thread or a bayonet mount, to which the needle can be affixed, is formed at the proximal end of the product container. A cap can be detachably pushed onto the product container holder. At the proximal, i.e., rear, end of the housing 4, a metering member 3, rotatable relative to the housing 4 and forming an outer surface of the device, is arranged; the metering member can be gripped by the user of the device and is rotatable relative to the housing 4. A rotation of the metering member 3 in a first rotational direction causes an increase of the dose, while a rotation of the metering member in a second rotational direction causes a reduction of the dose. The metering member 3 is connected axially fixedly to the housing 4. The housing 4 has an annular groove 4b, into which an annular ridge 3d on the inner circumference of the metering member snaps, whereby the metering member is connected rotatably and axially fixedly to the housing 4.

In the region of the proximal end of the housing 4, a zero-dose mating stop 4c for a zero-dose stop 10c of a dose display element 10 is formed. The zero-dose mating stop 4c is formed resiliently on an arm, particularly because of simplified assembly.

An actuating element 7 equipped as an actuating button arranged at the proximal end of the drive and metering device can be pressed, in particular in the distal direction, by the user in order to discharge the product. The actuating element 7 is arranged relative to the metering member 3 such that it does not change its axial position during dose setting. In particular, the actuating element 7 is arranged in the metering member 3 so as to be displaceable by an actuation stroke length. The actuating element 7 can be actuated against the force of a preloaded reset spring 12, designed as a coil spring and acting as a compression spring. The reset spring 12 is supported on the product container holder 5, alternatively on the product container 14, and on a sleeve-like clamping piece 16, which will be referred to below as a clamping sleeve 16. The clamping sleeve 16 is displaced from a clamping or retaining position into a release position by the actuation by the actuating element 7. The spring 12, and in particular the actuating element 7 as well, resets the clamping sleeve 16 from the reset position to the clamping or retaining position.

The clamping sleeve 16 is connected axially fixedly to a sleeve-like bearing element 9, which has an external thread 9a and, by means of a recess 9b, engages with the housing 4 so as to be secured against secured against rotation and movable axially. The bearing element 9 is thus movable together with the clamping sleeve 16 along the longitudinal axis L. Between the actuating element 7 and the bearing element 9, a clutch element 2 is arranged, which is connected, in particular permanently, by a groove-like recess 2a rotationally fixedly and movable axially to a ridge 1a of a sleeve-like rotation element 1 so that the clutch element 2 rotates along with a rotation of the rotation element 1. The clutch element 2 loosely abuts, at its distal end, against the proximal end of the bearing element 9. The clutch element 2, at the proximal end thereof, has a third clutch structure 2b, in the form of toothing that extends over the circumference. The third clutch structure 2b is part of a clutch 2b, 3b, which connects the metering member 3 secured against rotation to the clutch element 2 when the clutch 2b, 3b is engaged, i.e., the third clutch structure 2b is engaged with a fourth clutch structure 3b, which is formed by the metering member 3. When the clutch 2b, 3b is disengaged, the clutch element 2 is rotatable relative to the metering member 3.

The actuating element 7, particularly the at least one catch member 7a thereof, abuts against the proximal end of the sleeve-like clutch element 2, whereby an actuation of the actuating element 7 causes a displacement of the clutch sleeve 2 in the distal direction and thus also a displacement of the sleeve-like bearing element 9 and the clamping sleeve 16 in the distal direction.

The dose display element 10, equipped as a dose display sleeve, has a spiral or helical dose scale 10a turning multiple times around the surface of the sleeve, the dose scale being formed from a plurality of concatenated dose values, indicated in particular in international units (IU). For example, the dose scale 10a can have settable dose values from 0 to 60 or 80 IU in increments of one or two. The product dose to be discharged can be set by rotating the metering member 3 relative to the housing 4 or the indicating means 4d, wherein the corresponding dose value can be read at the indicating means 4d or appears in the indicating means 4d.

In particular, the dose display element 10 is permanently rotationally fixed and axially movable relative to the clutch element 2, wherein the ridge 1a of the rotation element 1 extends through the groove like recess 2a of the clutch element 2 and engages rotationally fixedly and axially movable in a longitudinal guide of the dose display element 10.

The dose display element 10 has an internal thread 10d, which engages with the external thread 9a of the bearing element 9 in order that the dose display element 10 can be screwed along the bearing element 9.

At the proximal end of the dose display element 10 there is toothing 10b, which is used to release the engagement of the at least one catch member 7a of the actuating element 7 that is engaged with the metering member 3, so that the actuating element 7 can be reset in the proximal direction, more particularly by means of the reset spring 12.

The third clutch structure 2b of the clutch element 2 is in rotationally fixed engagement with the fourth clutch structure 3b of the metering member 3, so that the clutch element 2 is rotated along with the metering member 3 during dose-setting, wherein the metering member 2 likewise rotates the rotation element 1 and the dose display element 10. In that way, the dose display element 10 is screwed along the bearing element 9, whereby the dose can be read in the indicating means 4d.

The rotation element 1 is connected rotatably but axially fixedly to the metering member 3 by means of the annular ridge 1c engaging in an annular groove 3c of the metering member 3. The rotatability of the rotation element 1 relative to the metering member 3 depends on the shifting state of the clutch 2b, 3b, the rotation element 1 being rotatable relative to the metering member 3 if the clutch 2b, 3b is disengaged, i.e., the actuating element 7 has been actuated, and non-rotatable if the clutch 2b, 3b has been engaged, i.e., the actuating element 7 is not actuated.

The metering member 3 has at least one ridge 3a, two ridges in this case, which are engaged, in particular permanently engaged, rotationally fixedly and displaceable axially with a groove like recess 13a of a metering sleeve 13. A rotation of the metering member 3 relative to the indicating means 4*d* effects a rotation or driving of the metering sleeve 13 in the corresponding direction.

The metering sleeve 13 has an internal thread 13*c*, which engages with an external thread 8*a* of a sleeve-like advancement member 8, so that the metering sleeve 13 can be screwed relative to the advancement member 8 along the advancement member 8 by means of a rotation.

The sleeve-like advancement member 8 has a groove 8*b* overlapping the external thread 8*a* and extending in the longitudinal direction L, wherein a guiding engagement member 4*g* formed by the housing 4 engages with the groove in such a manner that the advancement member 8 is rotationally fixed and axially movable relative to the housing 4. In the structure of the housing 4, formed as an internal sleeve, which also comprises the guiding engagement member 4*g*, the housing has a guide 4*f* that guides the advancement member 8 in the region of the external thread 8, more particularly laterally. This internal sleeve-like structure further comprises a resiliently arranged retaining engagement member 4*h*, which is secured with a spring arm on the guiding engagement member 4*g*. The clamping sleeve 16, held in the retaining possession thereof by the reset spring 12, holds the retaining engagement member 4*h* in an engagement with the advancement member 8 such that the advancement member 8 is blocked relative to the retaining engagement member 4*h* against a displacement in the distal direction along the longitudinal axis L. The clamping sleeve 16 has a surface, more particularly a conical surface, that holds the retaining engagement member 4*h* in the retaining engagement with the advancement member 8. For example, the bottom of the groove 8*b* can have toothing (e.g., labeled 8*c* in other embodiments) with which the retaining engagement member 4*h* is engaged.

A discharge spring 11, constructed as a coil spring and acting as a compression spring, is supported on the sleeve-like advancement member 8, more particularly at the distal end of the spring, which is so strongly preloaded that the energy stored therein is sufficient to discharge the entire product that can be discharged from the product container 14 by means of displacement of the piston, in particular in a plurality of individual discharges. The proximal end of the discharge spring 11 is supported on the metering member 3.

At its proximal end, the metering sleeve 13 has a first clutch structure 13*b* in the form of toothing, more particularly external toothing, arranged around the circumference. At its distal end, the rotation member 1 has a second clutch structure 1*b*, with which the first clutch structure 13*b* can be brought into a rotationally fixed engagement, whereby a clutch 1*b*, 13*b*, more particularly a display reset clutch, is formed. If the clutch 1*b*, 13*b* is engaged, the rotation element 1 is rotationally fixed relative to the metering sleeve 13, while the metering member 1 is rotatable relative to the metering sleeve 13 if the clutch 1*b*, 13*b* is disengaged.

The housing 4, particularly the internal sleeve thereof, forms a metering stop 4*k* for the metering sleeve 13, the distal end face of which can strike the metering stop 4*k*.

A display reset spring 18, which is configured as a coil spring and operates as a compression spring in the first embodiment, is arranged between the housing 4 and the dose display element 10. The pitch of the thread 9*a*, 10*d* is sufficiently large that no self-locking takes place between the dose display element 10 and the bearing element 9 if a force acting along the longitudinal axis L is applied to the dose display element 10 by means of the reset spring 18.

At its proximal end, the housing 4 has toothing 4*a*, with which a cam 15*a* of a slip clutch spring 15 engages, the spring being connected to the metering member 3 for conjoint rotation. The slip clutch spring 15 is an annular part, more particularly a metal part, which was produced by press-bending, for example. If the metering member 3 is rotated relative to the housing 4, the cam 15*a* is moved by the teeth of the toothing 4*a*, whereby an audible sound is generated during the dose-setting. In addition, the engagement of the cam 15*a* with the toothing 4*a* can form a slip clutch, more particularly a two-way slip clutch, which prevents the metering member 3 from rotating unintentionally due to the spring forces acting on the metering member 3.

The injection device is shown in an initial state in FIGS. 3*a*-3*d*, wherein the dose display element 10 assumes its initial or zero portion, so that the dose "00" appears in the indicating means 4*d*. The actuating element 7 has not been actuated. The clutch 2*b*, 3*b*, formed from third and fourth clutch structures 2*b*, 3*b*, is engaged. The retaining engagement member 4*h* is held by the clamping piece 16 in a retaining engagement with the advancement member 8.

In order to increase the product dose to be administered, the metering member 3 is rotated relative to the housing 4 or the indicating means 4*d* in a first rotational direction, the clutch element 2 being rotated along with the metering member 3 in the first rotational direction by means of the engaged clutch 2*b* 3*b*. The clutch element 2 turns the rotation element 1, whereby the dose display element 10 screws along the bearing element 9, which is rotationally fixed relative to the housing 4, and the display reset spring 18 is cocked. The rotation of the metering member 3 in the first rotational direction additionally causes the metering sleeve 13 to also rotate in the first rotational direction, the metering sleeve 13 screwing in the proximal direction along the advancement member 8 and forming a distance between the metering stop 4*k* and the metering sleeve 13 that corresponds to a total discharge stroke $H_g$ (FIGS. 4*c*; 10*c*; 16*c*). In the position of the metering sleeve 13 shown in FIG. 3*c*, more particularly when the zero dose or a very small dose such as 1 or 2 IU is set, the clutch 1*b*, 13*b* is disengaged. If the dose display element 10 is rotated out of its zero-dose position, more particularly past the dose of 1 or 2 IU, the first clutch structure 13*b* is displaced into engagement with the second clutch structure 1*b*, so that the clutch 1*b*, 13*b* is engaged.

When the metering sleeve 13 strikes against the metering stop 4*k*, in particular if the zero dose has been set or a product discharge has taken place, there is a distance between the second clutch structure 1*b* and the first clutch structure 13*b* along the longitudinal axis L that corresponds to a second partial discharge stroke $H_2$, which can sometimes be very small, only a few hundredths or tenths of a millimeter, for example. It is only important that the distance is sufficiently large that the clutch 1*b*, 13*b* is securely disengaged when the metering sleeve 13 strikes against the metering stop 4*k*.

By turning the metering member 3 in the first rotational direction, as previously stated, the distance that corresponds to the total discharge stroke $H_g$ is formed between the metering stop 4*k* and the metering sleeve 13, wherein the first clutch structure 13*b* overlaps the second clutch structure 1*b* along the longitudinal axis L by an amount that corresponds to a first partial discharge stroke $H_1$. While the second partial discharge stroke $H_2$ is constant, the first partial discharge stroke $H_1$ is variable, and corresponds to the set dose. In general: $H_g > H_1$; more particularly: $H_g - H_1 = H_2 \neq 0$ mm.

The state shown in FIGS. 4a-4d shows the injection device in a maximum-dose position of the display element 10, the maximum dose of 80 IU being readable in the indicating means 4d in this example. The set dose can be reduced or corrected by rotating the metering member 3 in the second direction, opposite the first direction, reducing the distance of the metering sleeve 13 from the metering stop 4k, and/or the amount by which the first and second clutch structures 1b, 13b overlap.

The actuating element 7 is actuated, more particularly pressed, in order to discharge the set product dose (FIGS. 5a-5d), the at least one catch member 7a (e.g., latching element) of the actuating element 7 shifting the clutch element 2 in the distal direction, whereby the clutch 2b, 3b is disengaged. The clutch element 2 drives the bearing element 9, thus displacing the clamping sleeve 16 in the distal direction under the force of the reset spring 12. Due to the displacement of the clamping sleeve 16, the retaining engagement element 4h is released, so that the axially fixed retaining engagement between the retaining engagement element 4h and the advancement member 8 is detached, whereby the cocked spring 11 pushes the advancement member 8 in the distal direction or discharge direction by the total discharge stroke $H_g$, i.e., far enough that the metering sleeve 13 strikes against the metering stop 4k. During the total discharge stroke $H_g$ of the advancement member 8, the metering sleeve 13 first moves by the first partial discharge stroke $H_1$, the clutch 1b, 3b being engaged during the first partial discharge stroke $H_1$, so that the rotation member 1 is rotationally fixed relative to the metering sleeve 13. Because the rotation element 1 is rotationally fixedly connected to the dose display element 10, the dose display element 10 is rotationally fixed relative to the indicating means 4d. At the end of the partial discharge stroke $H_1$, the clutch 1b, 13b is disengaged, the metering sleeve 13 then carrying out its second partial discharge stroke $H_2$ and finally striking the metering sleeve 4k. As soon as the clutch 1b, 13b is opened, the rotation element 1 is no longer rotationally fixed relative to the housing 4 or the indicating means 4d, whereby the dose display element 10 on the bearing element 9 is abruptly screwed back into its initial or zero-dose position due to the cocked reset spring 18 (FIGS. 5a-5d), the dose display element striking with its zero-dose stop 10c against the zero-dose mating stop 4c.

Upon reaching the initial or zero-dose position, the dose display element 10 releases the latching engagement by which the toothing 10b holds the actuating member 7 in the actuated position by means of the at least one catch member 7a, and thus the reset spring 12 resets the actuating member 7 into the unactuated position. During resetting of the actuating element 7 into its unactuated position, the reset spring 12 displaces the clamping sleeve 16 into the clamping or retaining position thereof, in which the clamping sleeve 16 presses the retaining engagement element 4h into an axially fixed engagement with the advancement member 8. At the same time, the bearing element 9 is displaced or reset in the proximal direction, together with the dose display element 10. The clutch element 2 is also reset, whereby the clutch 2b, 3b is engaged.

The device is now ready for another setting of a dose. By repeatedly setting and discharging the dose, the product contained in the product container 14 can be discharged in several total discharge strokes or multiple arbitrarily selectable individual doses.

FIGS. 6a-6d show the state of the drive and metering device in which the product container 14 contains a dischargeable amount of product that is less than the maximum dose settable by the drive and metering device. In the example shown, the product container 14 contains 78 IU, while a maximum of 80 IU can be set with the drive and metering device. To avoid improper usage, the driving and metering device comprises a limiting device that limits the dose-setting. For this purpose, the advancement member 8 comprises a stop at the proximal end of the thread 8a, against which the metering sleeve 13 strikes, thus blocking a rotation of the metering member 3 in the first rotational direction, even if an optionally provided maximum-dose stop is not in contact with a corresponding maximum-dose mating stop. A rotation of the metering member 3 in the second rotational direction is possible, however, i.e., in a rotational direction that causes a down-metering or a reduction of the dose.

In the second embodiment, shown in FIGS. 7-12d, the actuating element 7 is designed such that it must be held in the actuated position by the user in order discharge the product, i.e., it is not interlocked in an actuating position with the metering member 3. This has the effect that the user of the device can interrupt the injection process. Of course, it is alternatively possible to provide a mechanism in the second embodiment that holds the metering member 7 in its actuated position, such as the mechanism from the first embodiment.

The metering member 3 has a rod-like guiding means, which is surrounded by the discharge spring 11 and prevents lateral buckling of the discharge spring 11. This guiding means can also be provided for the other embodiments described herein.

Differing from the first embodiment, the at least one retaining engagement member 4h is not formed by the housing 4, but rather by a gripping ring 17 received axially fixedly in the housing 4 and having, in the example shown, four retaining engagement members 4h and an annular spring 17a, the retaining engagement members 4h being distributed around the circumference of the annular spring 17a and fastened to the annular spring 17a. The annular spring 17a can be made of metal or plastic, for example. The gripping ring 17, including the annular spring 17a and the retaining engagement members 4h, can be an integrally produced injection molded plastic part, for example.

Alternatively, an annular spring 17a formed from metal can be provided, which is then overmolded by means of a plastic injection molding process with one or more retaining engagement members 4h, two to four, for example.

The clamping sleeve 16 has, on the inner circumference thereof, a conical surface 16a, which causes the clamping sleeve 16, movable back and forth between the retaining or clamping position and the release position, to press the retaining engagement members 4h into engagement with toothing 8c extending along the longitudinal axis of the advancement member 8 or to release them from the toothing 8c.

In other respects, the reader is referred to the description for the first embodiment.

The third embodiment, from FIGS. 13-18d, is constructed similarly to the second embodiment and, in the broadest sense, to the first embodiment as well.

In essence, the third embodiment differs from the first embodiment in that, instead of a display reset spring 18 acting as a compression spring, a display reset spring 18 acting as a torsion spring and designed as a coil spring is provided for resetting the dose display element 10 to its original or zero-dose position. For this purpose, the thread 9a can be, but need not necessarily be, provided with such a small pitch that self-locking would occur in case of an axial load.

The display reset spring 18 is supported for conjoint rotation at one end on the rotation element 1, or alternatively on the dose display element 10, and is supported rotationally fixedly on the housing 4 at the other end. A rotation of the metering member 3 in the first rotational direction tensions the display reset spring 18, while a rotation of the metering member 3 in the second direction relaxes the display reset spring 18.

The dose display element 10 does not have a zero-dose stop, but can have a zero-dose stop, as is the case in the first and second embodiments. The dose display element 10 has a maximum-dose stop 10e, which strikes a maximum-dose mating stop 4i, formed by the housing 4 for example, when a maximum dose is set, for example, 80 IU in this case. A rotation of the metering member 3 in the first rotational direction is then blocked, while a reduction of the dose, i.e., a rotation of the metering member 3 in the second rotational direction, is possible. Although not shown, the dose display element 10 of the first and second embodiments can have such a maximum dose stop 10e or maximum-dose mating stop 4i, in particular, as an alternative to or in addition to the zero-dose stop 10c.

Figure 13:
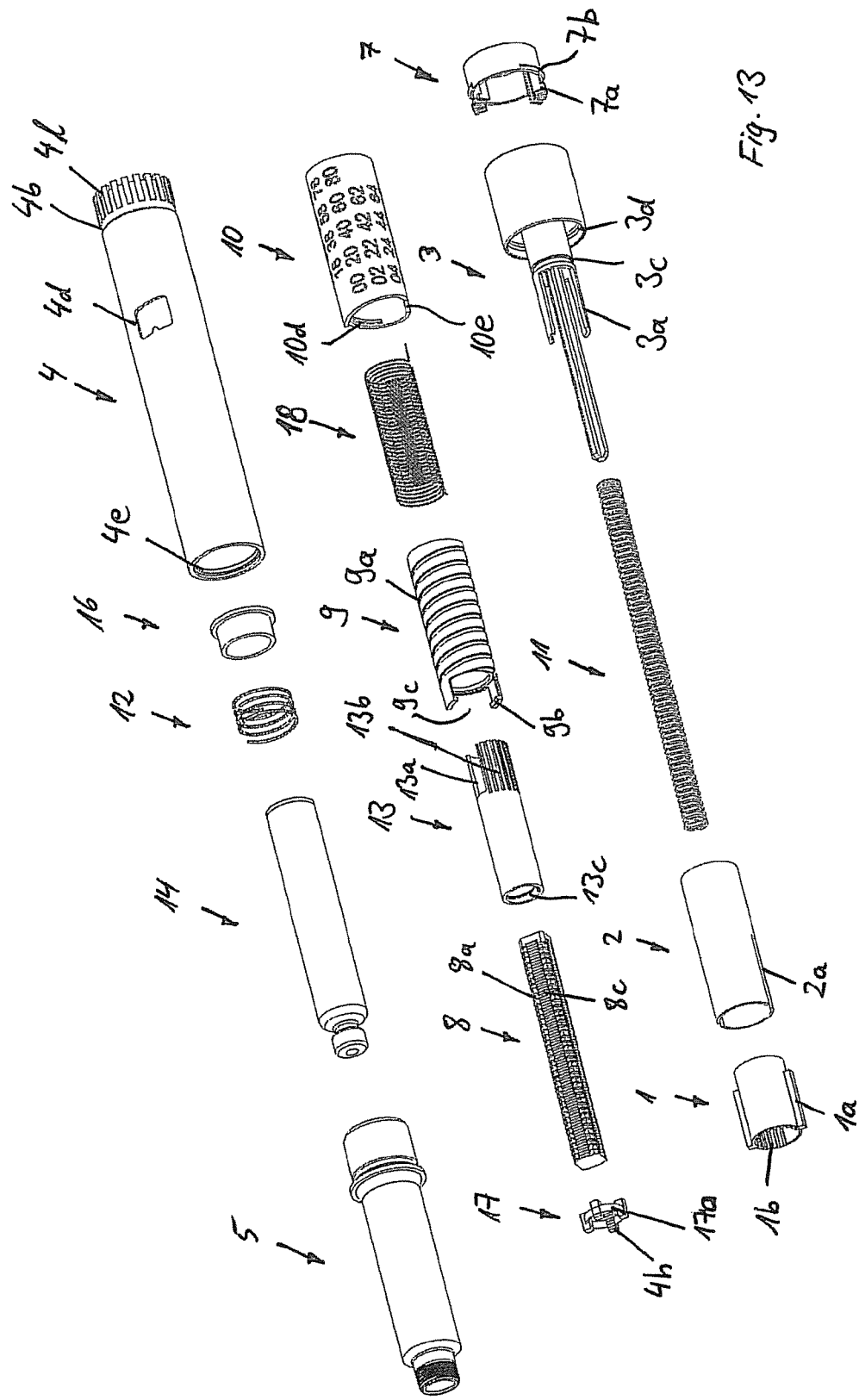
FIG. 13 shows an exploded view of an injection device having a drive and metering device according to a third embodiment.

FIGS. 13 and 14 show toothing 4l at the proximal end of the housing 4, with which the catch member 7a engages or can be coupled by actuation of the actuating element 7, so that the actuating element 7 and the metering member 3 are rotationally fixed relative to the housing 4 when the actuating element 7 has been actuated. The actuating element 7 has an annular ridge 7b, which is snapped during assembly over an annular ridge 3e of the metering member 3 and then strikes axially against the annular ridge 3e in order to prevent the actuating element 7 from dropping out of the metering member 3.

The invention claimed is:

1. A drive and metering device for an injection device for dispensing a liquid product, wherein a product dose to be discharged can be set with the drive and metering device, comprising:
    a dose display element comprising a dosage scale arranged over its circumference;
    an indicator;
    a metering member that can be gripped by a user of the drive and metering device;
    a discharge spring; and
    an advancement member,
    wherein the dose display element can be screwed relative to the indicator about a longitudinal axis (L) by rotating the metering member relative to the indicator to set a dose to be administered such that a value of the dose scale that corresponds to the set dose can be read via the indicator,
    wherein the discharge spring delivers stored energy to advance the advancement member in a discharge direction to discharge the product such that the advancement member is moved by a total discharge stroke ($H_g$) in the discharge direction, and
    wherein the total discharge stroke ($H_g$) comprises a first partial discharge stroke ($H_1$), during which the dose display element is rotationally fixed relative to the indicator, and after the first partial discharge stroke ($H_1$) the dose display element is rotatable relative to the indicator.

2. The drive and metering device of claim 1, wherein the total discharge stroke ($H_g$) comprises the first partial discharge stroke ($H_1$) and a second partial discharge stroke ($H_2$), and wherein the dose display element is rotatable relative to the indicator during the second partial discharge stroke ($H_2$).

3. The drive and metering device of claim 2, wherein the second partial discharge stroke ($H_2$) is constant.

4. The drive and metering device of claim 1, further comprising a display reset spring configured to rotate the dose display element back into a zero-dose position.

5. The drive and metering device of claim 4, wherein the display reset spring is cocked by rotating the metering member in a rotational direction that causes an increase of the dose.

6. The drive and metering device of claim 1, further comprising a bearing element rotationally fixed and axially movable relative to a housing of the drive and metering device, the bearing element comprising an external thread threadedly engaged with the dose display element such that the dose display element is screwable relative to the bearing element.

7. The drive and metering device of claim 6, further comprising an actuating element for actuating discharge of the product by causing the bearing element to be displaced relative to the indicator along the longitudinal axis (L).

8. The drive and metering device of claim 1, further comprising a clutch comprising a first clutch structure formed by a metering sleeve rotationally fixed and axially displaceable relative to the metering member, and a second clutch structure formed by a rotation element and coupled to the dose display element for enabling conjoint rotation and axial movement,
    wherein, in an engaged state, the clutch couples the indicator or a housing of the drive and metering device rotationally fixedly to the dose display element during the first partial discharge stroke ($H_1$), and
    wherein, in a disengaged state of the clutch, the indicator is rotationally decoupled from the dose display element such that the display element is rotatable relative to the indicator.

9. The drive and metering device of claim 1, wherein the discharge spring is preloaded and configured to discharge the product in a plurality of individual discharges.

10. The drive and metering device of claim 9, wherein the discharge spring is configured as a compression spring.

11. The drive and metering device of claim 1, wherein the advancement member is retained axially by a gripping device that is coupled rotationally fixedly and axially movably to a housing of the drive and metering device, the gripping device being in a releasable engagement with an external thread of the advancement member, wherein actuation of an actuating element for actuating discharge of the product causes the engagement of the gripping device with the advancement member to be released such that the advancement member is movable in the discharge direction.

12. The drive and metering device of claim 11, wherein the gripping device comprises a retaining engagement element formed by the housing or a gripping ring.

13. The drive and metering device of claim 1, further comprising a metering sleeve configured to engage with an external thread of the advancement member, wherein the metering sleeve can be screwed by rotating the metering member relative to the advancement member, wherein a metering distance between the metering sleeve and a metering stop is increased by rotating the metering member in a rotational direction that causes an increase of the dose.

14. The drive and metering device of claim 13, wherein the metering distance between the metering stop and the metering sleeve is reduced by rotating the metering member in a rotational direction that causes a reduction of the dose.

15. The drive and metering device of claim 13, wherein the metering distance between the metering sleeve and the metering stop corresponds to the total discharge stroke ($H_g$) of the advancement member.

16. The drive and metering device of claim 1, further comprising an actuating element for actuating discharge of the product, wherein upon actuation, the actuating element remains in an actuated position until a product discharge is finished, or until the dose display element has substantially rotated back into a starting or a zero-dose position.

17. The drive and metering device of claim 16, wherein upon actuation, the actuating element releasably interlocks with the metering member, and wherein the interlocking is releasable by the dose display element.

* * * * *